(12) United States Patent
Kennedy et al.

(10) Patent No.: US 10,526,590 B2
(45) Date of Patent: Jan. 7, 2020

(54) COMPOUNDS AND METHODS FOR CRISPR/CAS-BASED GENOME EDITING BY HOMOLOGOUS RECOMBINATION

(71) Applicant: Agilent Technologies, Inc., Santa Clara, CA (US)

(72) Inventors: Andrew Kennedy, Sunnyvale, CA (US); Gusti Zeiner, Pacifica, CA (US); Subhadeep Roy, Lafayette, CO (US); Chong Wing Yung, San Jose, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 346 days.

(21) Appl. No.: 15/251,235

(22) Filed: Aug. 30, 2016

(65) Prior Publication Data

US 2017/0058298 A1    Mar. 2, 2017

Related U.S. Application Data

(60) Provisional application No. 62/212,456, filed on Aug. 31, 2015.

(51) Int. Cl.
| | | |
|---|---|---|
| *C12N 9/22* | (2006.01) | |
| *C12N 15/11* | (2006.01) | |
| *C12N 15/113* | (2010.01) | |

(52) U.S. Cl.
CPC .................................... *C12N 9/22* (2013.01)

(58) Field of Classification Search
None
See application file for complete search history.

(56) References Cited

U.S. PATENT DOCUMENTS

| | | | |
|---|---|---|---|
| 5,032,401 | A | 7/1991 | Spiros et al. |
| 5,607,677 | A | 3/1997 | Spiros et al. |
| 7,371,580 | B2 | 5/2008 | Yakhini et al. |
| 8,202,983 | B2 | 6/2012 | Dellinger et al. |
| 9,580,727 | B1 * | 2/2017 | Donohoue |
| 2003/0003547 | A1 | 1/2003 | Dutreix et al. |
| 2005/0281781 | A1 | 12/2005 | Ostroff |
| 2010/0076183 | A1 | 3/2010 | Dellinger et al. |
| 2013/0330778 | A1 | 12/2013 | Zeiner et al. |
| 2014/0242664 | A1 * | 8/2014 | Zhang .................. C12N 15/902 435/188 |
| 2014/0273037 | A1 | 9/2014 | Wu |
| 2014/0273226 | A1 | 9/2014 | Wu |
| 2014/0273233 | A1 | 9/2014 | Chen et al. |
| 2014/0342458 | A1 | 11/2014 | Mali et al. |
| 2015/0031133 | A1 | 1/2015 | Church et al. |

FOREIGN PATENT DOCUMENTS

| | | |
|---|---|---|
| WO | 2013176772 A1 | 11/2013 |
| WO | 2013176844 A1 | 11/2013 |
| WO | 2014144592 A3 | 12/2014 |
| WO | 2014191521 A2 | 12/2014 |
| WO | 2015089486 A2 | 6/2015 |
| WO | 2014144761 A3 | 10/2015 |

OTHER PUBLICATIONS

Mali et al. Cas9 as a versatile tool for engineering biology, nature methods, vol. 10, No. 10, Oct. 2013, 957-963.*
Hendel, et al., "Chemically Modified Guide RNAs Enhance Crispr-cas Genome Editing in Human Primary Cells", Nature Biotechnology, vol. 33, No. 9, 6129/2015, 985-989.
Konermann, et al., "Genome-scale Transcriptional Activation by an Engineered CRISPR-Cas9 Complex", Nature, vol. 517, No. 7536, Dec. 10, 2014, 583-588.
Banga et al., Oligonucleotide-directed site-specific mutagenesis in *Drosophila melanogaster*. PNAS 89(5), 1735-9 (1992).
Bétermier et al., Is non-homologous end-joining really an inherently error-prone process? PLoS Genetics, 10(1), e1004086 (2014).
Bibikova et al., Enhancing gene targeting with designed zinc finger nucleases. Science 300(5620), 764 (2003).
Cho et al. (Seoul National Univ.), Targeted genome engineering in human cells with the CAS9 RNA-guided endonuclease, Nat. Biotechnol. Mar. 2013, Supplementary Information.
Cong et al., Multiplex Genome Engineering Using CRISPR/Cas Systems, Science. Feb. 15, 2013; 339(6121):819-23.
Dellinger et al., Streamlined Process for the Chemical Synthesis of RNA Using 20-O-Thionocarbamate-Protected Nucleoside Phosphoramidites in the Solid Phase, J. Am. Chem. Soc. 2011, 133, 11540-11556.
Fu et al., Improving CRISPR-Cas nuclease specificity using truncated guide RNAs, Nat. Biotechnol., 32, 279-84 (2014).
Gaj, et al., ZFN, TALEN, and CRISPR/Cas-based methods for genome engineering, Trends in Biotech 31(7):307 (2013).
Gold et al., Aptamer-Based Mutiplexed Proteomic Technology for Biomarker Discovery. PLOS ONE 5(12)e15004 (2010).
Hsu et al., Development and Applications of CRISPR-Cas9 for Genome Engineering. Cell, 157(6), 1262-1278 (2014).
Hwang and Fu et al., Efficient In Vivo Genome Editing Using RNA-Guided Nucleases, Nat Biotechnol. Mar. 2013; 31(3):227-9.
Jinek et al., RNA-programmed genome editing in human cells, Elife 2, e00471 (2013).
Jinek et al., A Programmable Dual-RNA-Guided DNA Endonuclease in Adaptive Bacterial Immunity, Science 2012; 337:816-821.
Kass et al., Double-strand break repair by homologous recombination in primary mouse somatic cells requires BRCA1 but not the ATM kinase, (Proc Natl Acad Sci USA. 110(14): 5564-5569 (2013)).
Li et al., Multiplex and homologous recombination-mediated genome editing in *Arabidopsis* and *Nicotiana benthamiana* using guide RNA and Cas9, (Nat Biotechnol. (8):688-91 (2013)).

(Continued)

*Primary Examiner* — Channing S Mahatan

(57) ABSTRACT

The present invention relates to guide RNAs comprising adaptor segments having one or more modifications, and their use in homologous recombination by CRISPR:Cas systems. The modified adaptor segments are resistant to degradation by RNaseH. The present invention also relates to a dual guide RNA strategy in which a first guide RNA directs a Cas enzyme to make a double-strand break at a first target sequence, and a second guide RNA comprises an adaptor segment attached to a donor polynucleotide, and binds a second target sequence that is offset from the first target sequence.

20 Claims, 6 Drawing Sheets

Specification includes a Sequence Listing.

(56) References Cited

OTHER PUBLICATIONS

Lujambio et al., Genetic Unmasking of an Epigenetically Silenced micro RNA in Human Cancer Cells, (Spanish National Cancer Centre) Cancer Res. Feb. 2007, 67:1424-1429.
Mali et al, RNA-Guided Human Genome Engineering via CAS9, Science, Feb. 15, 2013; 339(6121):823-6.
Mali et al., CAS9 transcriptional activators for target specificity screening and paired nickases for cooperative genome engineering. Nature Biotechnology 31, 833-838(2013).
Mandal et al., Efficient ablation of genes in human hematopoietic stem and effector cells using CRISPR/Cas9. Cell Stem Cell. Nov. 6;15(5):643-52 (2014).
Miller et al., A TALE nuclease architecture for efficient genome editing. Nature Biotechnology, 29(2), 143-82011 (2011).
Nussbaum et al., Restriction-stimulated homologous recombination of plasmids by the RecE pathway of *Escherichia coli*. Genetics, 130(1), 37-49 (1992).
Puchta et al., Homologous recombination in plant cells is enhanced by in vivo induction of double-strand breaks into DNA by a site-specific endonuclease. Nucleic Acids Research, 21(22), 5034-40 (1993).
Qi et al., Increasing frequencies of site-specific mutagenesis and gene targeting in *Arabidopsis* by manipulating DNA repair pathways (Genome Res 23:547-554 (2013)).
Kumar, et al., Template-Directed Oligonucleotide Strand Ligation, Covalent Intramolecular DNA Circularization and Catenation Using Click Chemistry, Journal of the American Chemical Society, 2007, 129, 6859-6864.
Ran et al., Double Nicking by RNA-Guided CRISPR Cas9 for Enhanced Genome Editing Specificity. Cell, 154(6), 1380-1389 (2013).
Rouet et al., Expression of a site-specific endonuclease stimulates homologous recombination in mammalian cells. PNAS 91(13), 6064-6068 (1994).
Ruff, et al., Aptamer-guided gen targeting in years and human cells. Nucleic Acids Res. 42(7):e61, 2014.
Storici et al., Chromosomal site-specific double-strand breaks are efficiently targeted for repair by oligonucleotides in yeast. PNAS 100(25), 14994-9 (2003).
Vasquez et al., Manipulating the mammalian genome by homologous recombination. PNAS 98(15), 8403-10 (2001).
Yamada et al., Synthesis and Biochemical Evaluation of Phosphonoformate Oligodeoxyribonucleotides, J. Am. Chem. Soc. 128(15), 5251-5261 (2006).
Yu et al., A new method for detecting sites of 2'-O-methylation in RNA molecules. RNA 3(3): 324-331 (1997).
PCT, "International Search Report and Written Opinion dated Dec. 23, 2016", Application No. PCT/US2016/049468, 13 pages.
Extended European Search Report dated Feb. 20, 2019, Application No. 16842808.4, 7 pages.
Inoue, Hideo et al., Sequence-Dependent Hydrolysis of RNA using Modified Oligonucleotide Splints and RNase H, FEBS Letters, Elsevier, Amsterdam, Nl, vol. 215, No. 2, May 11, 1987, 327-330.

* cited by examiner

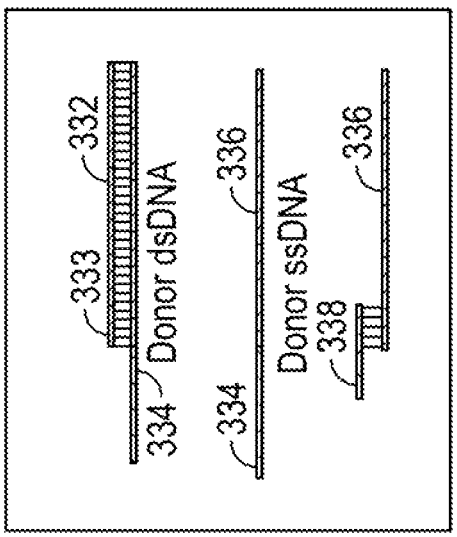
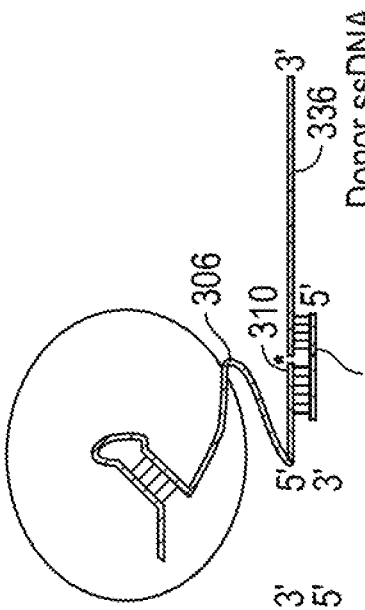
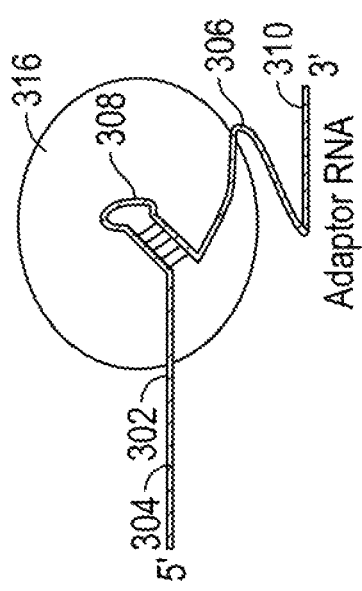
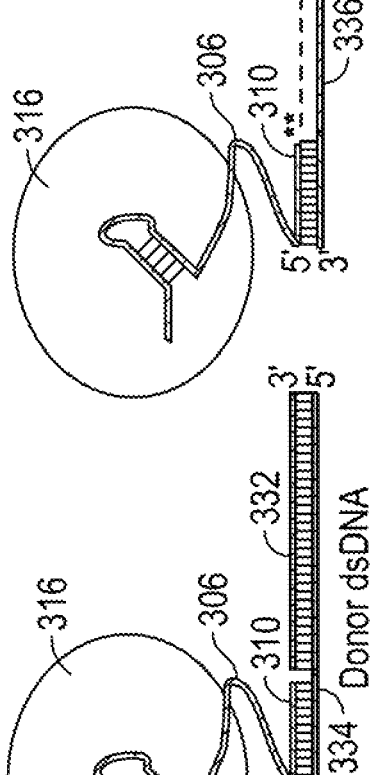
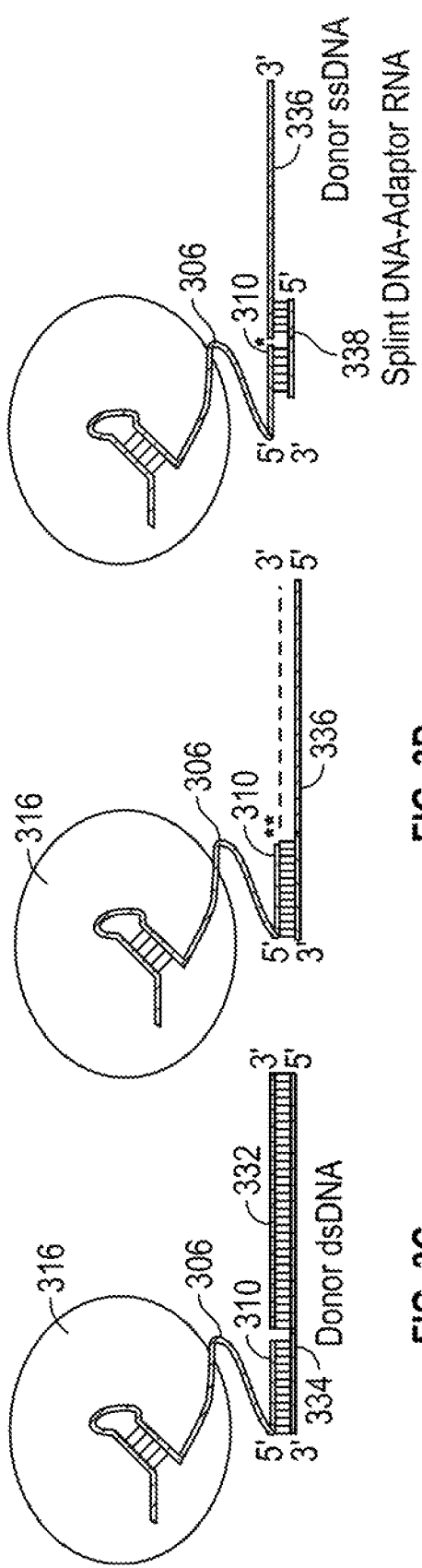
FIG. 3A
FIG. 3B
FIG. 3C
FIG. 3D
FIG. 3E

SEQUENCE LISTING

```
<160> NUMBER OF SEQ ID NOS: 1

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30
```

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
 50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

```
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                    485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
                690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
                770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
```

```
Gly Lys Ser Asp Asn Val Pro Ser Glu Glu Val Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260
```

| | | | | | | | | | | | | |
|---|---|---|---|---|---|---|---|---|---|---|---|---|
| His | Tyr 1265 | Leu | Asp | Glu | Ile 1270 | Ile | Glu | Gln | Ile | Ser 1275 | Glu | Phe | Ser | Lys |
| Arg | Val 1280 | Ile | Leu | Ala | Asp 1285 | Ala | Asn | Leu | Asp | Lys 1290 | Val | Leu | Ser | Ala |
| Tyr | Asn 1295 | Lys | His | Arg | Asp 1300 | Lys | Pro | Ile | Arg | Glu 1305 | Gln | Ala | Glu | Asn |
| Ile | Ile 1310 | His | Leu | Phe | Thr 1315 | Leu | Thr | Asn | Leu | Gly 1320 | Ala | Pro | Ala | Ala |
| Phe | Lys 1325 | Tyr | Phe | Asp | Thr 1330 | Thr | Ile | Asp | Arg | Lys 1335 | Arg | Tyr | Thr | Ser |
| Thr | Lys 1340 | Glu | Val | Leu | Asp 1345 | Ala | Thr | Leu | Ile | His 1350 | Gln | Ser | Ile | Thr |
| Gly | Leu 1355 | Tyr | Glu | Thr | Arg 1360 | Ile | Asp | Leu | Ser | Gln 1365 | Leu | Gly | Gly | Asp |

COMPOUNDS AND METHODS FOR CRISPR/CAS-BASED GENOME EDITING BY HOMOLOGOUS RECOMBINATION

CROSS-REFERENCE TO RELATED APPLICATIONS

This application claims benefit of the filing date of and right of priority to U.S. Provisional Application No. 62/212,456, filed Aug. 31, 2015, the contents of which are incorporated herein by reference.

FIELD OF THE INVENTION

The present invention relates to the field of molecular biology. In particular, the present invention relates to the use clusters of regularly interspaced short Lalindromic repeats (CRISPR) technology for homologous recombination.

BACKGROUND OF THE INVENTION

The native prokaryotic CRISPR/Cas system comprises an array of short repeats with intervening variable sequences of constant length (i.e., clusters of regularly interspaced short palindromic repeats, or "CRISPR"), and CRISPR-associated ("Cas") proteins. The RNA of the transcribed CRISPR array is processed by a subset of the Cas proteins into small guide RNAs, which generally have two components as discussed below. There are at least three different systems: Type I, Type II and Type III. The enzymes involved in the processing of the RNA into mature crRNA are different in the 3 systems. In the native prokaryotic system, the guide RNA ("gRNA") comprises two short, non-coding RNA species referred to as CRISPR RNA ("crRNA") and trans-acting RNA ("tracrRNA"). In an exemplary system, the gRNA forms a complex with a Cas nuclease. The gRNA:Cas nuclease complex binds a target DNA sequence having a protospacer adjacent motif ("PAM") and a protospacer. The protospacer is complementary to a target DNA, and the gRNA is also complementary to at least a portion of the target DNA. The recognition and binding of the target DNA by the gRNA:Cas nuclease complex induces cleavage of the target DNA. The native CRISPR/Cas system functions as adaptive immune system in prokaryotes, as gRNA:Cas nuclease complexes recognize and silence exogenous genetic elements, thereby conferring resistance to exogenous genetic elements such as plasmids and phages.

It has been demonstrated that a single guide RNA ("sgRNA") can replace the complex formed between the naturally-existing crRNA and tracrRNA. Considerations relevant to developing a gRNA, including a sgRNA, include specificity, stability, and functionality. Specificity refers to the ability of a particular gRNA:Cas nuclease complex to bind to and/or cleave a desired target, whereas little or no binding and/or cleavage of polynucleotides different (in sequence and/or location) from the desired target occurs. Thus, specificity refers to minimizing off-target effects of the gRNA:Cas nuclease complex. Stability refers to the ability of the gRNA to resist degradation by enzymes, such as nucleases, and other substances that exist in intra-cellular and extra-cellular environments. There is a need for providing gRNA, including sgRNA, having increased resistance to nuclease degradation, increased binding affinity for the target DNA, and/or reduced off-target effects while, nonetheless, having gRNA functionality.

Targeted gene editing has potential for functional gene analysis and for gene therapy applications. Approaches that introduce double-stranded breaks (DSBs) at defined target sites have improved the frequency of genome editing via homologous recombination (HR) of exogenous donor polynucleotide templates. Banga et al., Oligonucleotide-directed site-specific mutagenesis in *Drosophila melanogaster*. PNAS 89(5), 1735-9 (1992); Nussbaum et al., Restriction-stimulated homologous recombination of plasmids by the RecE pathway of *Escherichia coli*. Genetics, 130(1), 37-49 (1992); Puchta et al., Homologous recombination in plant cells is enhanced by in vivo induction of double-strand breaks into DNA by a site-specific endonuclease. Nucleic Acids Research, 21(22), 5034-40 (1993); Rouet et al., Expression of a site-specific endonuclease stimulates homologous recombination in mammalian cells. PNAS 91(13), 6064-81994 (1994); Storici et al., Chromosomal site-specific double-strand breaks are efficiently targeted for repair by oligonucleotides in yeast. PNAS 100(25), 14994-9 (2003). These approaches include engineered homing endonucleases, zinc finger nucleases (Bibikova et al., Enhancing gene targeting with designed zinc finger nucleases. Science 300(5620), 764 (2003)), transcription activator-like effector nucleases (TALENS) (Miller et al., A TALE nuclease architecture for efficient genome editing. Nature Biotechnology, 29(2), 143-82011 (2011)), and RNA-guided Cas9 nucleases (Hsu et al., Development and Applications of CRISPR-Cas9 for Genome Engineering. Cell, 157(6), 1262-1278 (2014)) to induce DSBs at defined genomic target sites. With these nuclease-mediated gene targeting approaches, a primary limitation is the low frequency with which HR occurs at the DSB relative to the frequency of non-homologous end joining (NHEJ) (Bétermier et al., Is non-homologous end-joining really an inherently error-prone process? PLoS Genetics, 10(1), e1004086 (2014)). In mammalian cells, NHEJ is the favored DSB repair modality by three orders of magnitude, with one successful HR and NHEJ event occurs per $10^5$-$10^7$ and $10^2$-$10^4$ treated cells, respectively (Vasquez et al., Manipulating the mammalian genome by homologous recombination. PNAS 98(15), 8403-10 (2001)).

Genome editing methods that increase the frequency of HR relative to NHEJ after a DSB is induced, and even to favor HR over NHEJ, are desired. To facilitate this, researchers have proposed guiding exogenous donor polynucleotides templates to the vicinity of the DSB by tethering the donor to a DNA aptamer that is bound by a homing endonuclease (I-SceI). Thus, the genome-editing agent carries the HR repair template to the site of the genetic modification, which will increase the local concentration of the HR template at the genomic repair site. Using this approach, HR was improved 16- and 32-fold, in human and yeast cells, respectively (Ruff, et al., Aptamer-guided gen targeting in years and human cells. Nucleic Acids Res. 42(7):e61, 2014). However, with the homing endonuclease approach, the landscape of target genomic sequences is constrained, limited by the specific 18 DNA base-pair target recognition site of the (Ice-I) endonuclease. Although it is conceivable to select new DNA aptamers to extend this strategy for use with different homing endonucleases, aptamer selection has proven to be a difficult process in practice. (Gold et al., Aptamer-Based Mutiplexed Proteomic Technology for Biomarker Discovery. PLOS ONE 5(12)e15004 2010) Additionally, engineering homing endonucleases, zinc finger nucleases and transcriptional activator-like nucleases to target novel DNA sequences remains challenging (Gaj, et al., ZFN, TALEN, and CRISPR/Cas-based methods for genome engineering. Trends in Biotech 31(7):307 (2013).

Homologous gene targeting approaches have been used to knock out endogenous genes or knock-in exogenous sequences in the chromosome. They can also be used for gene correction, and in theory, for the correction of mutations linked with monogenic diseases. However, this application is difficult, due to the low efficiency of the process. For example, Mali et al. (Science 339:823-826 (2013)) attempted gene modification in human K562 cells using CRISPR (guide RNA and Cas9 endonuclease) and a concurrently supplied single-stranded donor DNA, and observed an HDR-mediated gene modification at the AAVS1 locus at a frequency of 2.0%, whereas NHEJ-mediated targeted mutagenesis at the same locus was observed at a frequency of 38%. Li et al. (Nat Biotechnol. (8); 688-91 (2013)) attempted gene replacement in the plant *Nicotiana benthamiana* using CRISPR (guide RNA and Cas9 endonuclease) and a concurrently supplied double-stranded donor DNA, and observed an HDR-mediated gene replacement at a frequency of 9.0%, whereas NHEJ-mediated targeted mutagenesis was observed at a frequency of 14.2%. Li et al. also tested the possibility of enhancing HDR in *Nicotiana benthamiana* by triggering ectopic cell division, via co-expression of *Arabidopsis* CYCD3 (Cyclin D-Type 3), a master activator of the cell cycle; however, this hardly promoted the rate of HDR (up to 11.1% from 9% minus CYCD3). Kass et al. (Proc Natl Acad Sci USA. 110(14): 5564-5569 (2013)) studied HDR in primary normal somatic cell types derived from diverse lineages, and observed that mouse embryonic and adult fibroblasts as well as cells derived from mammary epithelium, ovary, and neonatal brain underwent HDR at I-SceI endonuclease-induced DSBs at frequencies of approximately 1% (0.65-1.7%). Kass and others have reported higher HDR activity when cells are in S and G2 phases of the cell cycle. Strategies to improve HDR rates have also included knocking out the antagonistic NHEJ repair mechanism. For example, Qi et al. (Genome Res 23:547-554 (2013)) reported an increase of 5-16 fold in HDR-mediated gene targeting in *Arabidopsis* for the ku70 mutant and 3-4 fold for the lig4 mutant. However, the overall rates were observed to be no higher than ~5%, with most less than 1%. Furthermore, once the desired gene-targeting event was produced, the ku70 or lig4 mutations had to be crossed out of the mutant plants.

Mali, et al. US20140342458 discusses a method of altering a eukaryotic cell by transfecting the cell with a nucleic acid encoding RNA complementary to genomic DNA of the cell, transfecting the cell with a nucleic acid encoding an enzyme that interacts with the RNA and cleaves the genomic DNA in a site specific manner. The cell expresses the RNA and the enzyme, the RNA binds to complementary genomic DNA, and the enzyme cleaves the genomic DNA in a site specific manner. It states that gRNAs are flexible to sequence insertions on the 5' and 3' ends (as measured by retained HR inducing activity), and ssDNA donors may be tethered to gRNAs via hybridization, thus enabling coupling of genomic target cutting and immediate physical localization of repair template which can promote homologous recombination rates over error-prone non-homologous end-joining. See also Church et al. US20150031133.

Dutreix et al. US20030003547 discusses methods and compositions for gene alternation or repair based on oligonucleotide-directed triple helix formation and homologous recombination. It states that triple helix-forming oligonucleotides (TFOs) had been chosen to guide homologous donor DNA (DD) to an intended target site on genomic DNA and to position it for efficient information transfer via homologous recombination and/or gene conversion. In this approach, TFO is covalently tethered to DD through a linker. It states that the effectiveness of the TFO-DD conjugate could be explained by: (i) an increase in the local concentration of DD; and (ii) a stimulation of DNA repair by triple helix formation that could provoke recruitment of proteins involved in homologous pairing, strand exchange and/or recombination. US20030003547 provides an approach where a homing device (TFO) and a donor DNA (DD) are joined together by non-covalent interaction through an adapter oligonucleotide, which is covalently linked to TFO. It states that an oligonucleotide (natural and modified oligonucleotide (ODN), or RNA-DNA chimeric oligonucleotide (RDO)), or also a small DNA fragment (either single- or double-stranded) could be guided the target site for homologous replacement.

BRIEF DESCRIPTION OF THE DRAWINGS

FIG. 3A shows an adaptor RNA sequence appended on the 3' end of a guide RNA bound to a Cas 9 protein. FIG. 3B shows three examples of different topologies of donor DNA oligonucleotides that can be tethered to the guide RNA by an adaptor segment. FIGS. 3C, 3D and 3E illustrate strategies for tethering guide RNA to a donor DNA for potential HR.

DETAILED DESCRIPTION OF THE INVENTION

Figure 1:
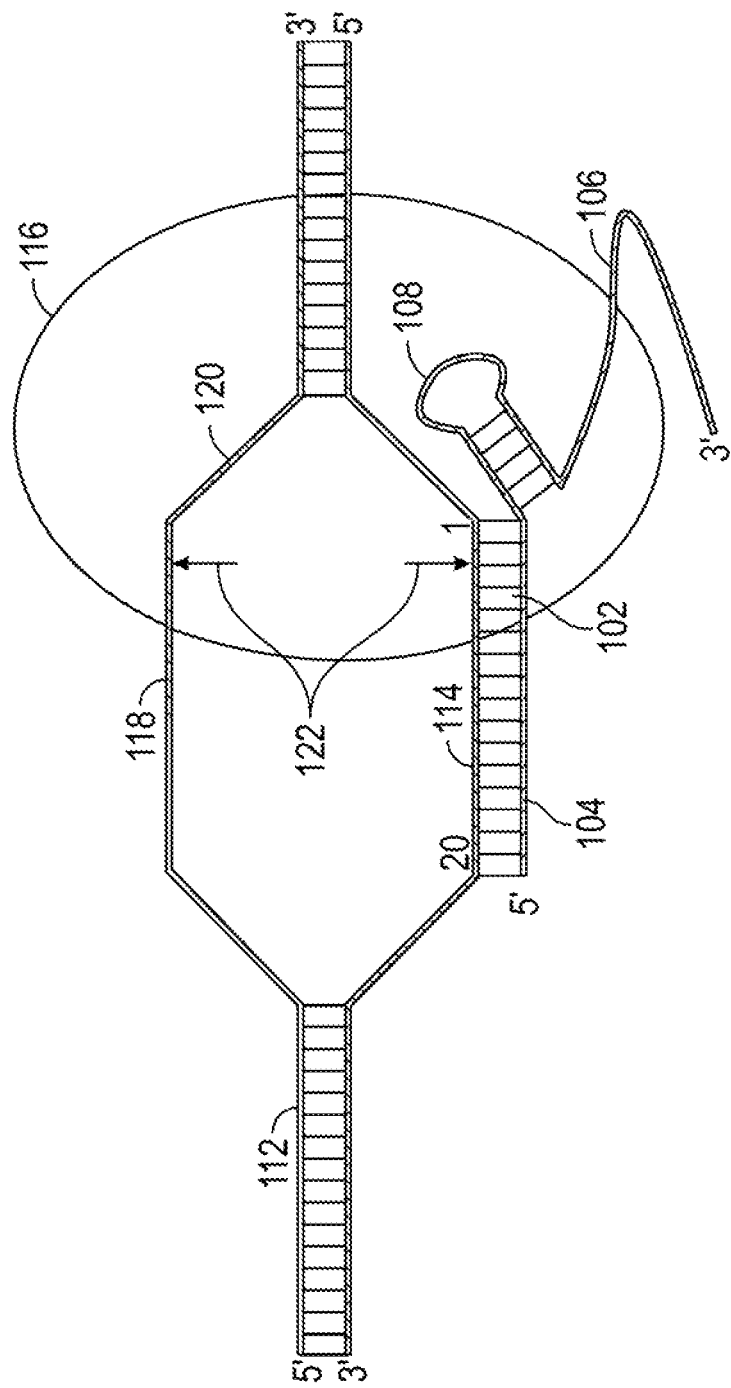
FIG. 1 illustrates CRISPR-Cas9 mediated, sequence specific cleavage of DNA.

This invention relates to compounds and methods for modifying a target polynucleotide by homologous recombination using a Cas protein:guide RNA system. The present disclosure provides guide RNAs comprising adaptor segments for attaching donor polynucleotides, other adaptors, or splint segments. In certain embodiments, modifications to the adaptor segment increase the stability of the adaptor:donor polynucleotide complex; and do not substantially compromise the efficacy of Cas:gRNA binding to, nicking of, and/or cleavage of the target polynucleotide. In certain embodiments, a dual Cas:gRNA system is used in which a first guide RNA directs a Cas protein to make a double-strand break at a first target sequence, and a second guide RNA comprises an adaptor segment tethered to a donor polynucleotide. The second guide RNA binds a second target sequence that is offset from the first target sequence.

I. Definitions

As used herein, the term "guide RNA" generally refers to an RNA molecule (or a group of RNA molecules collectively) that can bind to a Cas protein and aid in targeting the Cas protein to a specific location within a target polynucleotide (e.g., a DNA). A guide RNA can comprise a crRNA segment and a tracrRNA segment. As used herein, the term "crRNA" or "crRNA segment" refers to an RNA molecule or portion thereof that includes a polynucleotide-targeting guide sequence, a stem sequence, and, optionally, a 5'-overhang sequence. As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The term "guide RNA" encompasses a single guide RNA (sgRNA), where the crRNA segment and the tracrRNA segment are located in the same RNA molecule. The term "guide RNA" also encompasses, collectively, a group of two or more RNA molecules, where the crRNA segment and the tracrRNA segment are located in separate RNA molecules.

The term "nucleic acid", "polynucleotide" or "oligonucleotide" refers to a DNA molecule, an RNA molecule, or analogs thereof. As used herein, the terms "nucleic acid", "polynucleotide" and "oligonucleotide" include, but are not limited to DNA molecules such as cDNA, genomic DNA or synthetic DNA and RNA molecules such as a guide RNA, messenger RNA or synthetic RNA. Moreover, as used herein, the terms "nucleic acid" and "polynucleotide" include single-stranded and double-stranded forms.

The term "modification" in the context of an oligonucleotide or polynucleotide includes but is not limited to (a) end modifications, e.g., 5' end modifications or 3' end modifications, (b) nucleobase (or "base") modifications, including replacement or removal of bases, (c) sugar modifications, including modifications at the 2', 3', and/or 4' positions, and (d) backbone modifications, including modification or replacement of the phosphodiester linkages. The term "modified nucleotide" generally refers to a nucleotide having a modification to the chemical structure of one or more of the base, the sugar, and the phosphodiester linkage or backbone portions, including nucleotide phosphates.

As used more generally herein, "modification" refers to a chemical moiety, or portion of a chemical structure, which differs from that found in unmodified ribonucleotides, namely adenosine, guanosine, cytidine, and uridine ribonucleotides. The term "modification" may refer to type of modification. For example, "same modification" means same type of modification, and "the modified nucleotides are the same" means the modified nucleotides have the same type(s) of modification while the base (A, G, C, U, etc.) may be different. Similarly, an adaptor with "two modifications" is a guide RNA with two types of modifications, which may or may not be in the same nucleotide, and each type may appear in multiple nucleotides in the adaptor. Similarly, an adaptor polynucleotide with "three modifications" is an adaptor with three types of modifications, which may or may not be in the same nucleotide, and each type may appear in multiple nucleotides.

A "donor polynucleotide" is a nucleotide polymer or oligomer intended for insertion at a target polynucleotide. The donor polynucleotide may be a natural or a modified polynucleotide, a RNA-DNA chimera, or a DNA fragment, either single- or double-stranded, or a PCR amplified ssDNA or dsDNA fragment. A fully double-stranded donor DNA is advantageous since it might provide an increased stability, since dsDNA fragments are generally more resistant than ssDNA to nuclease degradation.

The terms "xA", "xG", "xC", "xT", or "x(A,G,C,T)" and "yA", "yG", "yC", "yT", or "y(A,G,C,T)" refer to nucleotides, nucleobases, or nucleobase analogs as described by Krueger et al., "Synthesis and Properties of Size-Expanded DNAs: Toward Designed, Functional Genetic Systems", Acc. Chem. Res. 2007, 40, 141-150 (2007), the contents of which is hereby incorporated by reference in its entirety.

The term "Unstructured Nucleic Acid" or "UNA" refers to nucleotides, nucleobases, or nucleobase analogs as described in U.S. Pat. No. 7,371,580, the contents of which is hereby incorporated by reference in its entirety.

The terms "PACE" and "thioPACE" refer to internucleotide phosphodiester linkage analogs containing phosphonoacetate or thiophosphonoacetate groups, respectively. These modifications belong to a broad class of compounds comprising phosphonocarboxylate moiety, phosphonocarboxylate ester moiety, thiophosphonocarboxylate moiety and thiophosphonocarboxylate ester moiety. These linkages can be described respectively by the general formulae $P(CR_1R_2)_n COOR$ and $(S)-P(CR_1R_2)_n COOR$ wherein n is an integer from 0 to 6 and each of $R_1$ and $R_2$ is independently selected from the group consisting of H, an alkyl and substituted alkyl. Some of these modifications are described by Yamada et al., "Synthesis and Biochemical Evaluation of Phosphonoformate Oligodeoxyribonucleotides", J. Am. Chem. Soc. 128(15), 5251-5261 (2006), the contents of which is hereby incorporated by reference in its entirety.

As used herein, the term "target polynucleotide" or "target" refers to a polynucleotide containing a target nucleic acid sequence. A target polynucleotide may be single-stranded or double-stranded, and, in certain embodiments, is double-stranded DNA. In certain embodiments, the target polynucleotide is single-stranded RNA. A "target nucleic acid sequence" or "target sequence," as used herein, means a specific sequence or the complement thereof that one wishes to bind to, nick, or cleave using a CRISPR:Cas system.

The term "hybridization" or "hybridizing" refers to a process where completely or partially complementary polynucleotide strands come together under suitable hybridization conditions to form a double-stranded structure or region in which the two constituent strands are joined by hydrogen bonds. As used herein, the term "partial hybridization" includes where the double-stranded structure or region contains one or more bulges or mismatches. Although hydrogen bonds typically form between adenine and thymine or adenine and uracil (A and T or A and U) or cytosine and guanine (C and G), other noncanonical base pairs may form (See e.g., Adams et al., The Biochemistry of the Nucleic Acids, 11th ed., 1992). It is contemplated that modified nucleotides may form hydrogen bonds that allow or promote hybridization.

The term "cleavage" or "cleaving" refers to breaking of the covalent phosphodiester linkage in the ribosylphosphodiester backbone of a polynucleotide. The terms "cleavage" or "cleaving" encompass both single-stranded breaks and double-stranded breaks. Double-stranded cleavage can occur as a result of two distinct single-stranded cleavage events. Cleavage can result in the production of either blunt ends or staggered ends.

The term "CRISPR-associated protein" or "Cas protein" refers to a wild type Cas protein, a fragment thereof, or a mutant or variant thereof. The term "Cas mutant" or "Cas variant" refers to a protein or polypeptide derivative of a wild type Cas protein, e.g., a protein having one or more point mutations, insertions, deletions, truncations, a fusion protein, or a combination thereof. In certain embodiments, the "Cas mutant" or "Cas variant" substantially retains the nuclease activity of the Cas protein. In certain embodiments, the "Cas mutant" or "Cas variant" is mutated such that one or both nuclease domains are inactive. In certain embodiments, the "Cas mutant" or "Cas variant" has nuclease activity. In certain embodiments, the "Cas mutant" or "Cas variant" lacks some or all of the nuclease activity of its wild-type counterpart.

A synthetic guide RNA that has "gRNA functionality" is one that has one or more of the functions of naturally occurring guide RNA, such as associating with a Cas protein, or a function performed by the guide RNA in association with a Cas protein. In certain embodiments, the functionality includes binding a target polynucleotide. In certain embodiments, the functionality includes targeting a Cas protein or a gRNA:Cas protein complex to a target polynucleotide. In certain embodiments, the functionality includes nicking a target polynucleotide. In certain embodiments, the functionality includes acting within a gRNA:Cas system to cleave a target polynucleotide. In certain embodiments, the functionality includes associating with or binding to a Cas protein. In certain embodiments, the functionality is any other known function of a guide RNA in a CRISPR/Cas system with a Cas protein, including an artificial CRISPR/Cas system with an engineered Cas protein. In certain embodiments, the functionality is any other function of natural guide RNA. The synthetic guide RNA may have gRNA functionality to a greater or lesser extent than a naturally occurring guide RNA. In certain embodiments, a synthetic guide RNA may have greater functionality as to one property and lesser functionality as to another property in comparison to a similar naturally occurring guide RNA.

As used herein, the term "segment" of a sequence refers to any portion of the sequence (e.g., a nucleotide subsequence or an amino acid subsequence) that is smaller than the complete sequence. Segments of polynucleotides can be any length, for example, at least 5, 10, 15, 20, 25, 30, 40, 50, 75, 100, 150, 200, 300 or 500 or more nucleotides in length. A portion of a guide sequence can be about 50%, 40%, 30%, 20%, 10% of the guide sequence, e.g., one-third of the guide sequence or shorter, e.g., 7, 6, 5, 4, 3, or 2 nucleotides in length.

The term "derived from" in the context of a molecule refers to a molecule isolated or made using a parent molecule or information from that parent molecule. For example, a Cas9 single mutant nickase and a Cas9 double mutant null-nuclease are derived from a wild-type Cas9 protein.

The term "substantially identical" in the context of two or more polynucleotides (or two or more polypeptides) refers to sequences or subsequences that have at least about 60%, at least about 70%, at least about 80%, at least about 90%, about 90-95%, at least about 95%, at least about 98%, at least about 99% or more nucleotide (or amino acid) sequence identity, when compared and aligned for maximum correspondence using a sequence comparison algorithm or by visual inspection. Preferably, the "substantial identity" between polynucleotides exists over a region of the polynucleotide at least about 50 nucleotides in length, at least about 100 nucleotides in length, at least about 200 nucleotides in length, at least about 300 nucleotides in length, at least about 500 nucleotides in length, or over the entire length of the polynucleotide. Preferably, the "substantial identity" between polypeptides exists over a region of the polypeptide at least about 50 amino acid residues in length, at least about 100 amino acid residues in length, or over the entire length of the polypeptide.

As disclosed herein, a number of ranges of values are provided. It is understood that each intervening value, to the tenth of the unit of the lower limit, between the upper and lower limits of that range is also specifically contemplated. Each smaller range or intervening value encompassed by a stated range is also specifically contemplated. The term "about" generally refers to plus or minus 10% of the indicated number. For example, "about 10%" may indicate a range of 9% to 1%, and "about 20" may mean from 18-22. Other meanings of "about" may be apparent from the context, such as rounding off, so, for example "about 1" may also mean from 0.5 to 1.4.

II. CRISPR-Mediated Sequence-Specific Binding or Cleavage

FIG. 1 illustrates CRISPR-Cas9 mediated, sequence specific cleavage of DNA. A Cas9:guide RNA complex is shown with an engineered single guide RNA (sgRNA) having a 20 nucleotide (nt) 5' end 104 that matches the protospacer 118 of the target polynucleotide 112, followed by a Cas9 binding handle comprising a hairpin 108 and tracrRNA segment 106. An sgRNA may include more than one hairpin or loop. The gRNA forms a complex with a Cas9 nuclease 116. The Cas9:gRNA complex binds a target polynucleotide 112 containing the protospacer 118 directly upstream of a 3 nt protospacer adjacent motif (PAM) 120, with the 5' end 104 hybridizing with the target sequence 114. Cleavage occurs at both strands of the target polynucleotide at the cleavage sites 112 denoted by arrows (Jinek et al., A programmable dual-RNA-guided DNA endonuclease in adaptive bacterial immunity. Science 337(6096), 816-21 (2012)).

III. Guide RNAs

In at least one aspect, the present invention comprises a synthetic guide RNA that has guide RNA functionality and comprises an adaptor segment. In certain embodiments, the adaptor segment comprises a chemical modification, such as a stability-enhancing modification. A guide RNA that comprises a natural nucleotide with an unnatural substituent (e.g. a 2'-alkoxy or 2'-halo substituent), or any nucleotide other than the four canonical ribonucleotides, namely A, C, G, and U, whether unnatural or natural (e.g., a pseudouridine, inosine or a deoxynucleotide), comprises a modification. Likewise a guide RNA that comprises any backbone or internucleotide linkage other than a natural phosphodiester internucleotide linkage possesses a modification and therefore is a synthetic guide RNA comprising a modification.

In certain embodiments, the retained guide RNA functionality includes binding a Cas protein. In certain embodiments, the retained functionality includes binding a target polynucleotide. In certain embodiments, the retained functionality includes targeting a Cas protein or a gRNA:Cas protein complex to a target polynucleotide. In certain embodiments, the retained functionality includes nicking a target polynucleotide by a gRNA:Cas protein complex. In certain embodiments, the retained functionality includes cleaving a target polynucleotide by a gRNA:Cas protein complex. In certain embodiments, the retained functionality is any other known function of a guide RNA in a CRISPR/Cas system with a Cas protein, including an artificial CRISPR/Cas system with an engineered Cas protein. In certain embodiments, the retained functionality includes any other function of a natural guide RNA.

A. Guide RNA Comprising an Adaptor Segment

In certain embodiments, the guide RNA includes an adaptor segment. CRISPR guide RNAs with adaptor segments (e.g. segments of nucleic acids at the 3' end of the tracrRNA segment or the 5' end of the crRNA segment) can facilitate tethering of the guide RNA to polynucleotide sequences that can act as donors for homologous recombination (donor polynucleotides). When loaded with the guide RNA:donor polynucleotide complex, the Cas protein will bring the donor polynucleotide to a target cleavage site. This increases the local concentration of donor polynucleotide around the Cas cleavage site and increases the likelihood that a homologous recombination (HR) event will occur over other DNA repair mechanisms that do not require DNA donors. In the certain embodiments, extended sgRNAs are created with TC chemistry (discussed below), leaving a ssDNA or ssRNA 3' end exposed when Cas protein is bound to the sgRNA. New compositions (i.e., chemical modifications to the guide RNA) and designs (i.e., dual guide RNAs) are provided that will increase the feasibility of the 'chimeric' guide RNA:donor DNA approach to increase HR.

In certain embodiments, the adaptor segment is attached to the 5' end of the crRNA or to the 3' end of the tracrRNA, though there may be some portion where segments and/or functions overlap.

In certain embodiments, the adaptor segment of the guide RNA is at least 10 nucleotides, alternatively at least 11, 12, 13, 14, 15, 16, 17, 18, 19, 20, 22, 24, 26, 28, or 30 nucleotides in length. In certain embodiments, the adaptor segment of the guide RNA is at most 18, 19, 20, 22, 24, 26, 28, 30, 32, 34, 36, 38, or 40 nucleotides in length. Any of the foregoing minima and maxima may be combined to form a range, provided that the minimum is small than the maximum.

The flexibility of the programmable Cas9:guide RNA system can be employed to engineer specific DSB in the genome of a target cell (see FIG. 1), with the addition of tethered donor polynucleotides as templates for improved homologous recombination (see FIG. 3). In the present compositions and methods, a guide RNA is tethered to a specific donor polynucleotide at its 5' end, at a middle or interior portion, or at its 3' end, with the goal and effect of increasing the local concentration of the donor polynucleotide at the site of the double-stranded breaks created by a Cas9:gRNA complex. FIG. 3 provides several embodiments of this approach.

The 3' end of a guide RNA is not covered by the Cas9 protein, and there is evidence that modifying this 3' extension does not interfere with Cas9 activity. In certain embodiments, extended guide RNAs are created, leaving a ssDNA or ssRNA 3' end (an adaptor segment) exposed when Cas9 is bound to the guide RNA. This adaptor segment can be engineered to tether a donor polynucleotide in one of several configurations (either by direct attachment to the donor or via a second adaptor or a splint). In certain embodiments, the adaptor segment is attached at the 5' end of the donor polynucleotide, or to a middle or interior portion of the donor polynucleotide, or the 3' end of the donor polynucleotide. In certain embodiments, the adaptor segment (and the tethered donor polynucleotide) are located at positions other than the 3' end of the guide RNA, such as the 5' end of the gRNA or an overhang from the 5' end of the gRNA.

Figure 5A:
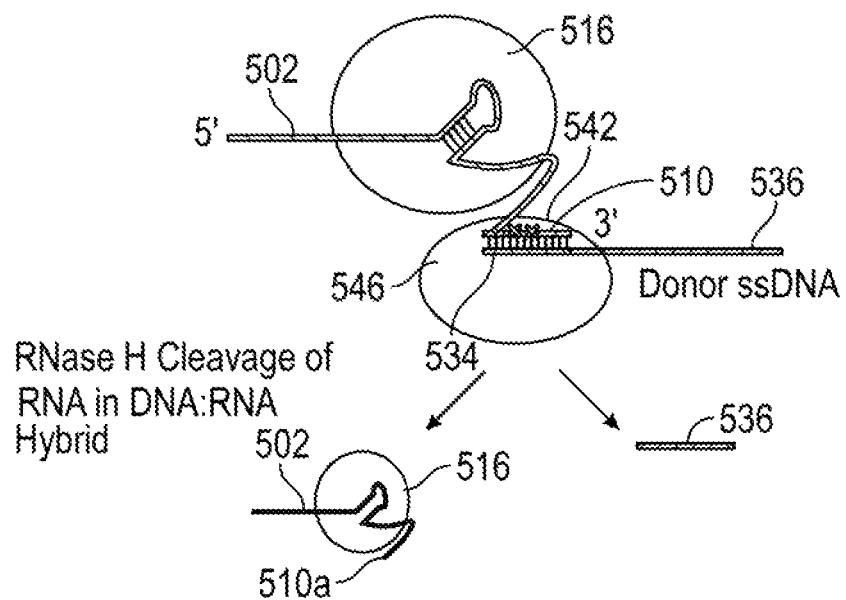
FIG. 5A shows the adaptor RNA:donor DNA duplex involves hybridization between the RNA adaptor sequence and donor DNA, in this instance, a short single-stranded DNA sequence.
Figure 5B:
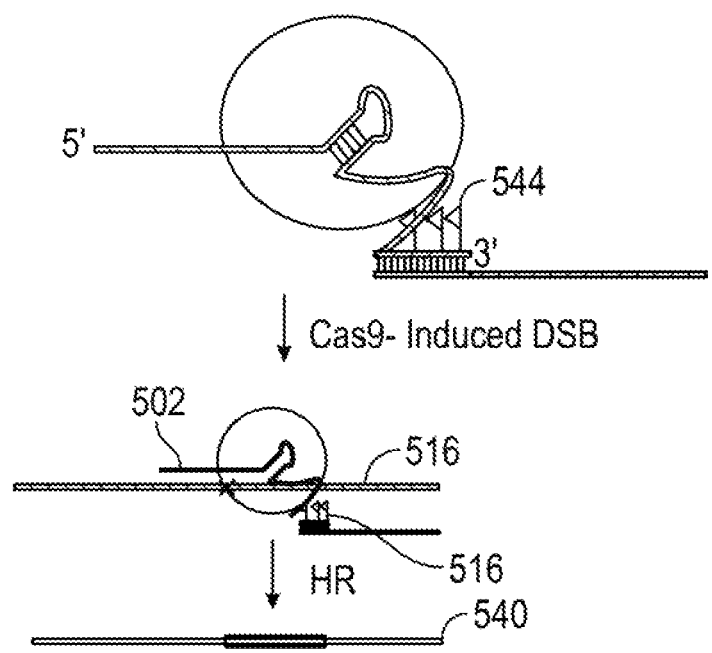
FIG. 5B shows a guide RNA adaptor sequence comprised of ribonucleotides with 2'-O-Methyl chemical modifications (flags) that prevent RNase H from cleaving the RNA:DNA hybrid formed between adaptor RNA and donor DNA.

The adaptor segment of the guide RNA comprises ssDNA or ssRNA adapted for hybridizing to a polynucleotide (e.g. a donor polynucleotide, a second adaptor segment, or a splint) through Watson Crick base-pairing. In the case of an ssRNA extension directly hybridized to a donor DNA, an adaptor RNA:donor DNA duplex is formed. Such a duplex is susceptible to nucleases, such as RNase H cleavage, of the RNA strand. An unmodified adaptor RNA:donor DNA duplex is susceptible to RNaseH cleavage, which is likely to sever the physical connection between guide RNA:Cas9 and the donor DNA, and donor DNA will not localize with Cas9 to the cut site (FIG. 5A). Furthermore, RNaseH cleavage may disrupt guide RNA/Cas9 functionality, degrade guide RNA and/or the donor DNA. To reduce the possibility of RNaseH cleavage and disruption of the adaptor RNA:donor DNA duplex, stability-enhancing modifications are introduced to the nucleotides in the adaptor segment of the guide RNA (FIG. 5B and described in more detail below). Modifications such as 2'-O-methyl have been proven to protect RNA in RNA:DNA hybrids from RNaseH cleavage (See Yu et al., A new method for detecting sites of 2'-O-methylation in RNA molecules. RNA 3(3): 324-331 (1997)). Different degrees and types of modifications to the guide RNA will yield a minimum and maximum number of modifications for prevention of RNaseH cleavage without impacting Cas activity and the desired recombination. Additional modifications known to stabilize guide RNA against phosphordiesterases and reduce the immunostimulatory properties of nucleic acids (i.e. 2'-O-methyl,3'phosphorothioate, 2'-O-methyl,3'thioPACE) could also be beneficial in the present components and methods.

FIGS. 3A to 3E illustrate some potential configurations for tethering guide RNA and donor polynucleotides. FIG. 3A shows an adaptor RNA sequence 310 appended on the 3' end of the guide RNA 306, which is bound to the Cas 9 protein 316. FIG. 3B shows three examples of different topologies of donor DNA oligonucleotides that can be tethered to the guide RNA by an adaptor segment. A double-stranded donor DNA 332 with a 5' overhang 333 (also referred to as a second adaptor segment) can be designed to directly hybridize with the adaptor 310 (shown in FIG. 3C). A DNA-RNA ligating enzyme can be used to ligate the DNA-RNA chimera at the junction indicated by *. A single-stranded donor DNA 336 (shown in FIG. 3D), with 3'→5' directionality, can also be designed to hybridize to the adaptor RNA 310, which can be extended to create a double-stranded donor DNA by DNA polymerase from RNA primer (site indicated by **). Alternatively, a single-stranded splint DNA 338 and donor DNA 336 can be designed such that when hybridized to the adaptor RNA (shown in FIG. 3E) the donor polynucleotide has the opposite directionality (5'→3') as in the previous configuration. The donor DNA 336 and adaptor RNA 310 can again be ligated with a DNA-RNA ligase (site of ligation indicated with *).

Another potential configuration has an adaptor segment attached (directly or indirectly) to a middle portion of the donor polynucleotide. In such a configuration, the portion of the donor polynucleotide attached to the adaptor segment (or to a splint) will generally include a portion of a gene, coding sequence or other sequence being inserted into the target polynucleotide to perform a desired function. Accordingly, the adaptor segment or a splint must be specially adapted for that portion. For example, the adaptor segment or splint has a nucleotide sequence complementary to a middle portion of the donor polynucleotide so that they will attach to each other by base-pair hybridization. In this configuration, an adaptor segment can be provided that specifically binds a given donor polynucleotide. In other configuration, such as where the donor polynucleotide is attached by its 5' end or 3' end to an adaptor segment, the 5' end or 3' end may comprise a portion that is not particular to the gene or sequence desired for introduction to the target polynucleotide, and the adaptor segment may be adapted to attach to a plurality of different donor polynucleotides having a common portion complementary to the adaptor segment.

The interaction between the adaptor segment and the donor polynucleotide may be covalent (by primer extension or by ligation), or it may be non-covalent. The splint may be a polynucleotide (including an oligonucleotide) consisting of nucleotides, or the splint may be a segment that comprise nucleic acids and other moieties, such as a peptide-nucleic acids or amino acids, or the split may be a polymer consisting of peptide-nucleic acids, or a protein or peptide consisting of natural or unnatural amino acids.

Figure 4:
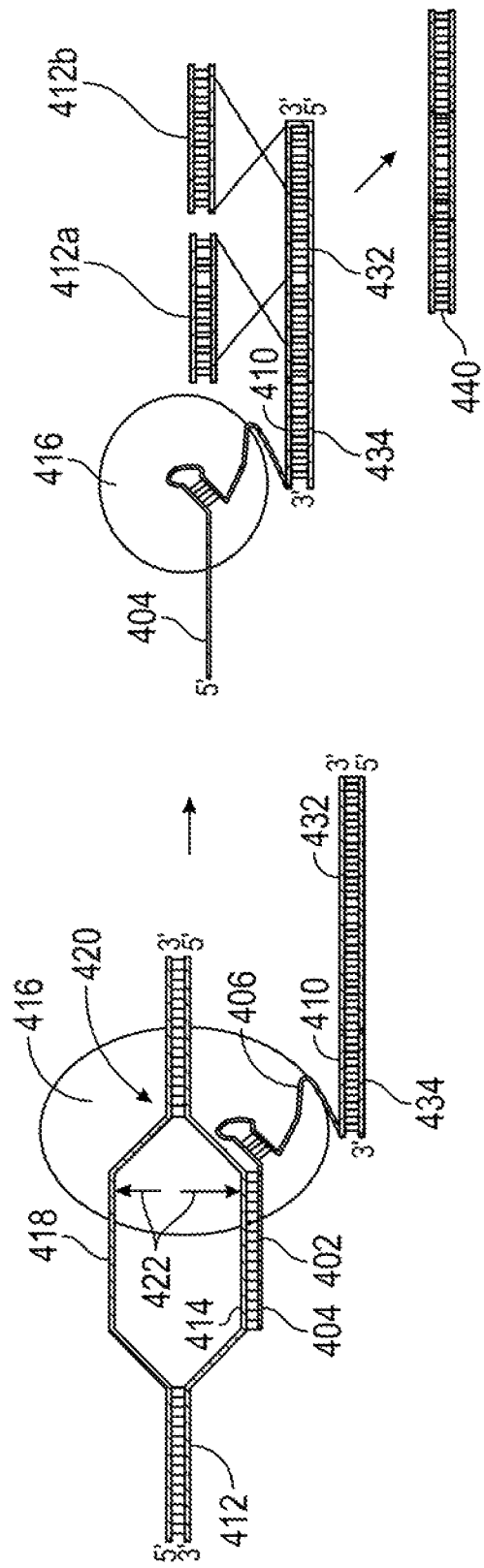
FIG. 4 shows a proposed donor DNA-tethered Cas9-mediated gene targeting.

FIG. 4 shows a proposed donor DNA-tethered Cas9-mediated gene targeting. (Left) The guide RNA 402 has a 20 nt 5' end 404 that matches the protospacer 418 of the target polynucleotide 412, followed by a Cas9 binding handle comprising a hairpin and tracrRNA segment 406. The guide RNA 402 includes an adaptor RNA 410 at the 3' end. The adaptor RNA 410 is hybridized to a double-stranded donor DNA 432 via a 5' overhang 434 (which may also be referred to as a second adaptor segment). The guide RNA 402 complexes with a Cas9 protein 416. The Cas9:gRNA complex binds a target polynucleotide 412 containing the protospacer 418 directly upstream of a 3 nt PAM 420, with the 5' end 404 hybridizing with the target sequence 414. The Cas9:guide RNA complex cleaves both strands of the target polynucleotide 412 at cleavage sites 422 denoted by arrows. After target polynucleotide cleavage, the Cas9-guide RNA complex remains in local proximity to the target polynucleotide which is now two segments 412a, 412b as a result of the double-stranded break (Right). This local proximity facilitates the likelihood of homologous recombination with donor polynucleotide 432 to form an edited polynucleotide 440.

B. Guide RNA Comprising an Adaptor Segment with at Least One Modification

In one aspect, the present technology provides a guide RNA comprising an adaptor segment having at least one modification, constituting a modified adaptor segment. In certain embodiments, the modification is a stability-altering modification. In certain embodiments, the modification increases nuclease resistance of the guide RNA relative to a guide RNA without the modification. In certain embodiments, the modification is a stability enhancing modification.

FIG. 5 illustrates chemical modifications protecting an adaptor RNA:donor DNA duplex from RNase H cleavage. Figure 5A shows the adaptor RNA:donor DNA duplex involves hybridization between the RNA adaptor sequence and donor DNA, in this instance, a short single-stranded DNA sequence. FIG. 5B shows a guide RNA adaptor sequence comprised of ribonucleotides with 2'-O-Methyl chemical modifications (flags) that prevent RNase H from cleaving the RNA:DNA hybrid formed between adaptor RNA and donor DNA. Stabilizing the chimeric guide RNA: donor DNA from RNase H degradation enables the donor DNA to be localized to the target site with the sgRNA:Cas9 protein.

In certain embodiments, the modified adaptor segment linked to the gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modifications. In certain embodiments, all the modifications are the same. In certain embodiments, all the modified nucleotides of the modified adaptor segment have the same type of modification. In certain embodiments, the modified adaptor comprises a combination of differently modified nucleotides. In certain embodiments, the modified adaptor segment comprises two or more modified nucleotides. In certain embodiments, the modified adaptor segment comprises three or more modified nucleotides. In certain embodiments, the modified nucleotides are arranged contiguously. In certain embodiments, the modified adaptor segment comprises at least one contiguous stretch of modified nucleotides. In certain embodiments, the modified adaptor segment comprises a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified nucleotides. Each modified nucleotide may independently comprise one or more types of modifications. In certain embodiments, no modified nucleotides are contiguous, or some but not all are contiguous, in the sequence of the modified adaptor segment.

In certain embodiments, the modification is a nucleotide sugar modification incorporated into the adaptor segment selected from the group consisting of 2'-O—C1-C4alkyl such as methyl ("2'-OMe"), 2'-deoxy (2'-H), 2'-OC1-C3alkyl-OC1-C3alkyl such as 2'-methoxyethyl ("2'-MOE"), 2' halo such as 2'-fluoro ("2'-F") or 2'-chloro ("21-C1"), 2'-amino ("2'-NH2"), 2'-arabinosyl ("2'-arabino") nucleotide, 2'-F-arabinosyl ("2'-F-arabino") nucleotide, 2'-locked nucleic acid ("LNA") nucleotide, 2'-unlocked nucleic acid ("ULNA") nucleotide, a sugar in L form ("L-sugar"), and 4'-thioribosyl nucleotide. In certain embodiments, the modification is an internucleotide linkage modification incorporated into the adaptor segment selected from the group consisting of: phosphorothioate "P(S)" (P(S)), phosphonocarboxylate (P(CH2)nCOOR) such as phosphonoacetate "PACE" (P(CH2COO—)), thiophosphonocarboxylate ((S)P (CH2)nCOOR) such as thiophosphonoacetate "thioPACE" ((S)P(CH2COO—)), alkylphosphonate (P(C1-C3alkyl) such as methylphosphonate —P(CH3), boranophosphonate (P(BH3)), and phosphorodithioate (P(S)2).

For example, in certain embodiments, the sugar comprises 2'-O—C1-4alkyl, such as 2'-O-methyl (2'-OMe). In certain embodiments, the sugar comprises 2'-O—C1-3alkyl-O—C1-3alkyl, such as 2'-methoxyethoxy (2'-O—CH2CH2OCH3) also known as 2'-O-(2-methoxyethyl) or 2'-MOE. In certain embodiments, the sugar comprises 2'-halo, such as 2'-F, 2'-Br, 2'-C1, or 2'-I. In certain embodiments, the sugar comprises 2'-NH2. In certain embodiments, the sugar comprises 2'-H (e.g., a deoxynucleotide). In certain embodiments, the sugar comprises 2'-arabino or 2'-F-arabino. In certain embodiments, the sugar comprises 2'-LNA or 2'-UNLA. In certain embodiments, the sugar comprises a 4'-thioribosyl. In certain embodiments, the modified adaptor segment comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified sugars.

In certain embodiments, the modification comprises a modified backbone (i.e., an internucleotide linkage other than a natural phosphodiester). Examples of modified internucleotide linkages include, but are not limited to, a phosphorothioate internucleotide linkage, a chiral phosphorothioate internucleotide linkage, a phosphorodithioate internucleotide linkage, a boranophosphonate internucleotide linkage, a $C_{1-4}$alkyl phosphonate internucleotide linkage such as a methylphosphonate internucleotide linkage, a boranophosphonate internucleotide linkage, a phosphonocarboxylate internucleotide linkage such as a phosphonoacetate internucleotide linkage, a phosphonocarboxylate ester internucleotide linkage such as a phosphonoacetate ester internucleotide linkage, a thiophosphonocarboxylate internucleotide linkage such as for example a thiophosphonoacetate internucleotide linkage, a thiophosphonocarboxylate ester internucleotide linkage such as a thiophosphonoacetate ester internucleotide linkage. Various salts, mixed salts and free acid forms are also included. In certain embodiments, the modified adaptor segment comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified internucleotide linkages.

In another aspect, the present technology provides an adaptor segment having a combination of two or more modifications. In certain embodiments, the modified nucleotide comprises a 2'-O-methyl,3'-phosphorothioate. In certain embodiments, the modified nucleotide comprises a 2'-O-methyl,3'-phosphonoacetate. In certain embodiments, the modified nucleotide comprises a 2'-O-methyl,3'-thiophosphonoacetate. In certain embodiments, the modified nucleotide comprises a 2'-halo,3'-phosphorothioate. In certain embodiments, the modified nucleotide comprises a 2'-halo,3'-phosphonoacetate. In certain embodiments, the modified nucleotide comprises a 2'-halo,3'-thiophosphonoacetate. In certain embodiments, the modified nucleotide comprises a 2'-fluoro,3'-phosphorothioate. In certain embodiments, the modified nucleotide comprises a 2'-fluoro,3'-phosphonoacetate. In certain embodiments, the modified nucleotide comprises a 2'-fluoro,3'-thiophosphonoacetate.

In certain embodiments, two or more modifications are on the same nucleotide (for example, one nucleotide comprises a 2'-O-methyl and a 3'thiophosphonoacetate moiety). In other embodiments, two or more modifications are on two different nucleotides (for example, one nucleotide has a 2'-flouro group and another nucleotide has a 2'-O-methyl group).

In certain embodiments, each modification in the adaptor segment is the same. In certain embodiments, at least one modification in the adaptor segment is different from at least one other modification in the adaptor segment. In certain embodiments, a single nucleotide within the adaptor segment possesses two or more modifications.

In certain embodiments, the adaptor segment comprises a combination of different types of modifications, and at least one type in the combination exists in multiple places in the adaptor polynucleotide. In certain embodiments, at least one type in the combination appears 1, 2, 3, 4, 5, 6, 7, 8, 9, 10, 11, 12, 13, 14, 15, 16, 17, 18, 19 or 20 times in the adaptor segment.

In certain embodiments, at least one type of the modifications in the combination appears in two or more modified nucleotides. In certain embodiments, at least one type of the modifications in the combination appears in three or more modified nucleotides. In certain embodiments, the modified nucleotides are not arranged contiguously in the sequence, or at least not entirely, as one or more unmodified nucleotides may intercede. In certain embodiments, the modified nucleotides are arranged contiguously. In certain embodiments, the adaptor polynucleotide comprises a stretch of contiguous modified nucleotides of the same type. In certain embodiments, the stretch has at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified nucleotides.

In certain embodiments, in addition to modifications in the adaptor polynucleotide, at least one type of modification is incorporated in the 5' portion or 3' portion of the guide RNA, particularly within the first 5 or 10 nucleotides of the 5' portion or within the last 5 or 10 nucleotides of the 3' portion to, for example, protect the RNA from degradation by nucleases or for other purposes. In certain embodiments, at least one type of the modifications in the combination is in the 5' portion and at least one type of the modifications in the combination is in the 3' portion of the guide RNA, particularly within the first 5 or 10 nucleotides of the 5' portion and within the last 5 or 10 nucleotides of the 3' portion in certain embodiments, at least one type of the modifications in the combination is within the internal region (i.e., between the 5' end and the 3' end) of the guide RNA. Modifications in portions other than the adaptor segment may be desired, for example, protect the RNA from degradation by nucleases or for other purposes.

In certain embodiments, at least one of the modifications in the combination comprises a 2'-O-methyl, a 2'-fluoro, a 2'-amino, a 2'-deoxy, a 2'-arabinosyl, a 2'-F-arabinosyl, a 3'-phosphorothioate, a 3'-phosphonoacetate, a 3'-phosphonoacetate ester, a 3'-thiophosphonoacetate, a 3'-thiophosphonoacetate ester, a 3'-methylphosphonate, a 3'-boranophosphonate, a 3-phosphorodithioate, or combinations thereof. In certain embodiments, at least one of the modifications in the combination comprises a 2'-O-methyl, a 2'-deoxy, a phosphorothioate internucleotide linkage, a phosphonoacetate internucleotide linkage, a thiophosphonoacetate internucleotide linkage, or combinations thereof. In certain embodiments, at least one of the modifications in the combination comprises a 2'-O-methyl, a 2'-deoxy, 2'-F, a phosphorothioate internucleotide linkage, a phosphonoacetate internucleotide linkage, a thiophosphonoacetate internucleotide linkage, or combinations thereof. In certain embodiments, at least two of the modifications in the combination comprise a 2'-O-methyl nucleotide and phosphorothioate internucleotide linkage, a 2'-O-methyl nucleotide and phosphonoacetate internucleotide linkage, or a 2'-O-methyl nucleotide and thiophosphonoacetate internucleotide linkage. In certain embodiments, at least two of the modifications in the combination comprise a 2'-O-methyl nucleotide and phosphonocarboxylate internucleotide linkage, a 2'-O-methyl nucleotide and phosphonocarboxylate ester internucleotide linkage, a 2'-O-methyl nucleotide and thiophosphonocarboxylate internucleotide linkage, a 2'-O-methyl nucleotide and thiophosphonocarboxylate ester internucleotide linkage, or combinations thereof.

In certain embodiments, at least one of the modifications in the combination comprises a 2'-O-methyl,3'-phosphorothioate. In certain embodiments, at least one of the modifications in the combination comprises a 2'-O-methyl,3'-phosphonoacetate. In certain embodiments, at least one of the modifications in the combination comprises a 2'-O-methyl,3'-thiophosphonoacetate. In certain embodiments, at least one of the modifications in the combination comprises a 2'-halo,3'-phosphorothioate. In certain embodiments, at least one of the modifications in the combination comprises a 2'-halo,3'-phosphonoacetate. In certain embodiments, at least one of the modifications in the combination comprises a 2'-halo,3'-thiophosphonoacetate. In certain embodiments, at least one of the modifications in the combination comprises a 2'-F,3'-phosphorothioate. In certain embodiments, at least one of the modifications in the combination comprises a 2'-F,3'-phosphonoacetate. In certain embodiments, at least one of the modifications in the combination comprises a 2'-F,3'-thiophosphonoacetate.

In certain embodiments, at least one of the modifications in the combination is a stability-altering modification. In certain embodiments, at least one of the modifications in the combination is a stability-enhancing modification. In certain embodiments, at least one of the modifications in the combination increases nuclease resistance of the guide RNA relative to a guide RNA without the modification.

In certain embodiments, at least one of the modifications in the combination alters stability and specificity of the guide RNA relative to a guide RNA without the modification. In certain embodiments, at least one of the modifications in the combination alters stability and transfection efficiency of the guide RNA relative to a guide RNA without the modification. In certain embodiments, at least one of the modifications in the combination alters specificity and transfection efficiency of the guide RNA relative to a guide RNA without the modification.

In certain embodiments, the combination includes at least one modification or a set of modifications that increases nucleases resistance (i.e., stability) with at least one modification or a set of modifications that increases specificity (i.e., reduce off-target effects). In certain embodiments, the combination includes at least one modification or a set of modifications that increases nucleases resistance (i.e., stability) with at least one modification or a set of modifications that raises the Tm of some bases pairing in the guide RNA. In certain embodiments, the combination includes at least one modification or a set of modifications that increases nucleases resistance (i.e., stability) with at least one modification or a set of modifications that lowers the Tm of some bases pairing of the guide RNA. In certain embodiments, the combination includes at least one modification or a set of modifications that increases nuclease resistance (i.e., stability), at least one modification or a set of modifications that increases the Tm of some bases paring in the guide RNA, and at least one modification or a set of modifications that decreases the Tm of some base paring elsewhere in the guide RNA. In certain embodiments, the combination includes at least one modification or a set of modifications that increases nuclease resistance (i.e., stability) and at least one modification or a set of modifications that increases the binding of the guide RNA with Cas protein. In certain embodiments, the combination includes at least one modification or a set of modifications that increases nuclease resistance (i.e., stability) and at least one modification or a set of modifications that increases the binding of the guide RNA with Cas protein. In certain embodiments, the guide RNA comprises a combination of the different types of modifications.

C. Guide RNA Structure

In certain embodiments, the guide RNA is able to form a complex with a CRISPR-associated-protein. In certain embodiments, the CRISPR-associated protein is, or is derived from, a CRISPR-Cas type II system, which has an RNA-guided nucleic acid-binding or nuclease activity. In certain embodiments, the CRISPR-associated protein is Cas9, a Cas9 mutant, or a Cas9 variant. In certain embodiments, the CRISPR-associated protein is the Cas9 nuclease from *Streptococcus pyogenes*. In certain embodiments, the CRISPR-associated protein is the Cas9 nuclease from *Streptococcus thermophilus*. In certain embodiments, the CRISPR-associated protein is the Cas9 nuclease from *Staphylococcus aureus*. In certain embodiments, the synthetic guide RNA or a synthetic guide RNA:CRISPR-associated protein complex maintains functionality of natural guide RNA or a complex that does not have modified nucleotides. In certain embodiments, the functionality includes binding a target polynucleotide. In certain embodiments, the functionality includes nicking a target polynucleotide. In certain embodiments, the functionality includes cleaving a target polynucleotide. In certain embodiments, the target polynucleotide is within a nucleic acid in vitro. In certain embodiments, the target polynucleotide is within the genome of a cell in vivo or in vitro (such as in cultured cells or cells isolated from an organism). In certain embodiments, the target polynucleotide is a protospacer in DNA.

In certain embodiments, the crRNA segment comprises from 25 to 80 nucleotides. In certain embodiments, the crRNA segment comprises a guide sequence that is capable of hybridizing to a target sequence. In certain embodiments, the guide sequence is complementary to the target sequence or a portion thereof. In certain embodiments, the guide sequence comprises from 15 to 30 nucleotides. In certain embodiments, the crRNA segment comprises a stem sequence. In certain embodiments, the stem sequence comprises from 10 to 50 nucleotides. In certain embodiments, the crRNA segment comprises a 5'-overhang sequence. In certain embodiments, the 5'-overhang sequence is attached to an adaptor segment. In certain embodiments, the 5'-overhang sequence comprises from 1 to 10 nucleotides. In certain embodiments, the crRNA comprises both (i) a guide sequence that is capable of hybridizing to a target sequence and (ii) a stem sequence. In certain embodiments, the crRNA comprises (i) a 5'-overhang sequence, (ii) a guide sequence that is capable of hybridizing to a target sequence, and (iii) a stem sequence. In certain embodiments wherein the crRNA segment comprises a stem sequence, the tracrRNA segment comprises a nucleotide sequence that is partially or completely complementary to the stem sequence of the crRNA segment. In certain embodiments, the tracrRNA segment comprises at least one more duplex structure.

The guide RNA comprises a 5' portion (i.e., the 5' half) and a 3' portion (i.e., the 3' half). In certain embodiments, the crRNA segment is 5' (i.e., upstream) of the tracrRNA segment. In certain embodiments, the tracrRNA segment is 5' relative to the crRNA segment.

In certain embodiments, the guide RNA comprises at least two separate RNA strands, for example, a crRNA strand and a separate tracrRNA strand. See, for example, FIG. 2A. In certain embodiments, the strands function together to guide binding, nicking, or cleaving of a target polynucleotide by a Cas protein, such as Cas9. In certain embodiments, the crRNA segment and the tracrRNA segment are on separate stands and hybridize to each other via two complementary sequences to form a stem or duplex.

In certain embodiments, the guide RNA is a single guide RNA comprising a crRNA segment and a tracrRNA segment. See, for example, FIG. 2B. In certain embodiments, the crRNA segment and the tracrRNA segment are connected by a loop sequence L. In certain embodiments, the loop L comprises 1, 2, 3, 4, 5, 6, 7, 8, 9, or 10 nucleotides. In certain embodiments, the loop L comprises a nucleotide sequence of GNRA, wherein N represents A, C, G, or U and R represents A or G. In certain embodiments, the loop L comprises a nucleotide sequence of GAAA. In certain embodiments, a single guide RNA comprises a 5' portion and a 3' portion, wherein the crRNA segment is upstream of the tracrRNA segment.

In certain embodiments, the total length of the two RNA pieces can be about 60-280 (e.g., about 60-260, 60-240, 65-280, 65-270, 65-260, 65-250, 65-240, 70-230, and 70-220) nucleotides in length, such as about 60, 65, 70, 75, 80, 90, 100, 110, 120, 130, 140, 150, 160, 170, 180, 190, 200, 220, 230, 240, 250, 260, 270 or 280 nucleotides in length. Similarly, the single guide RNA (e.g., FIG. 2B) can be about 60-280 (e.g., about 60-260, 60-240, 65-280, 65-270, 65-260, 65-250, 65-240, 70-230, and 70-220) nucleotides in length, such as about 60, 65, 70, 75, 80, 90, 100, 110, 120, 130, 140, 150, 160, 170, 180, 190, 200, 220, 230, 240, 250, 260, 270 or 280 nucleotides in length.

Figure 2A:
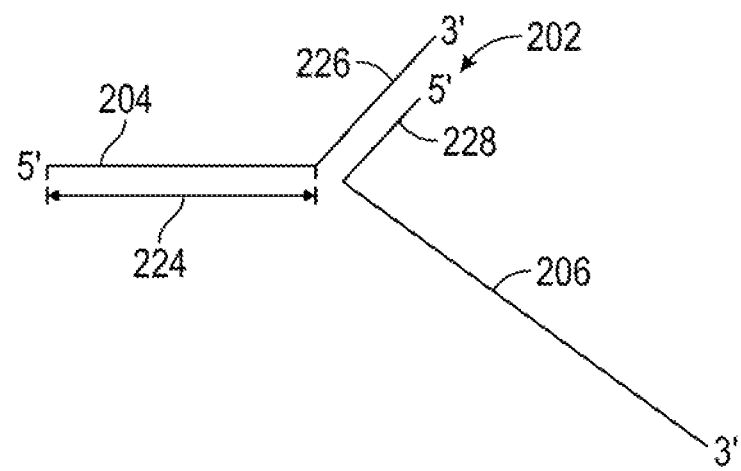
FIG. 2A illustrates a guide RNA comprising a crRNA segment and a separate tracrRNA segment.
Figure 2B:
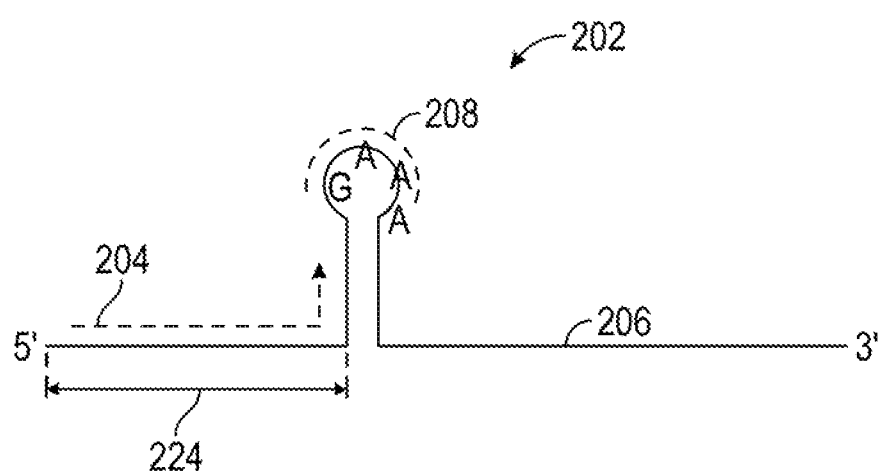
FIG. 2B illustrates a single guide RNA comprising a crRNA segment and a tracrRNA segment.

As shown in FIGS. 2A and 2B, the synthetic guide RNA comprises (i) a crRNA segment 204 that comprises (a) a guide sequence 224 capable of hybridizing to a target sequence in a nucleic acid, (b) a first stem sequence 226 capable of hybridizing partially or completely to a second stem sequence 228, and, optionally a 5'-overhang sequence and (ii) a tracrRNA segment 206 that comprises the second stem sequence 228. In certain embodiments, any nucleotide represented by O, G, X, Y, or T in the synthetic guide RNA shown in FIGS. 2A and 2B may be a modified nucleotide. The guide RNA shown in FIG. 2B represents a single guide RNA (sgRNA) where the crRNA segment and the tracrRNA segment are connected by a loop 230 having the sequence GAAA.

In certain embodiments, the crRNA segment of the guide RNA is 25-70 (e.g., 30-60, 35-50, or 40-45) nucleotides in length. In certain embodiments, the guide sequence is 12-30 (e.g., 16-25, 17-20, or 15-1.8) nucleotides in length. In some embodiments, a 5' portion of the crRNA does not hybridize or only partially hybridizes with the target sequence. For example, there can be a 5'-overhang on the crRNA segment.

In certain embodiments, the single guide RNA comprises a central portion including the stem sequence of the crRNA segment, the stem sequence of the tracrRNA segment, and, optionally, a loop that covalently connects the crRNA segment to the tracrRNA segment. In certain embodiments, the central segment of the single guide RNA is 8-60 (e.g., 10-55, 10-50, or 20-40) nucleotides in length.

In certain embodiments, the tracrRNA segment of the guide RNA is 10-130 (e.g., 10-125, 10-100, 10-75, 10-50, or 10-25) nucleotides in length. In certain embodiments, the tracrRNA segment includes one or more hairpin or duplex structures in addition to any hairpin or duplex structure in the central segment.

In certain embodiments, the tracrRNA segment is truncated compared to a reference tracrRNA, such as a naturally existing mature tracrRNA. A range of lengths has been shown to function in both the separate type (FIG. 2A) and the sgRNA type (FIG. 2B). For example, in certain embodiments, tracrRNA may be truncated from its 3' end by at least 1, 2, 3, 4, 5, 6, 7, 8, 9, 10, 15, 20, 25, 30, 35 or 40 nts. In certain embodiments, the tracrRNA molecule may be truncated from its 5' end by at least 1, 2, 3, 4, 5, 6, 7, 8, 9, 10, 15, 20, 25, 30, 35, 40, 45, 50, 55, 60, 65, 70, 75 or 80 nts. In certain embodiments, the tracrRNA molecule may be truncated from both the 5' and 3' end, e.g., by at least 1, 2, 3, 4, 5, 6, 7, 8, 9, 10, 15 or 20 nts from the 5' end and at least 1, 2, 3, 4, 5, 6, 7, 8, 9, 10, 15, 20, 25, 30, 35 or 40 nts from the 3' end. See, e.g., Jinek et al, Science 2012; 337:816-821; Mali et al, Science. 2013 Feb. 15; 339(6121):823-6; Cong et al, Science. 2013 Feb. 15; 339(6121):819-23; and Hwang and Fu et al, Nat Biotechnol. 2013 March; 31(3):227-9; Jinek et al, Elife 2, e00471 (2013)). In certain embodiments, the tracrRNA is untruncated. The tracrRNA segment has a sufficient number of nucleotides so that it retains tracrRNA functionality.

E. Donor Polynucleotide

A donor polynucleotide and adaptor RNA can be ligated with a DNA-RNA ligase to form a chimeric RNA-DNA where the adaptor is bound to the donor by an internucleotide linkage (at * in FIGS. 3C and 3E).

Using the present compositions and methods, donor polynucleotides may be inserted into a target polynucleotide, for example, into the genome of a cell. In certain embodiments, the donor polynucleotides are a double-stranded polynucleotide with sense and/or antisense strand polynucleotide overhangs that are at least partially complementary to corresponding polynucleotide overhangs of cleaved target polynucleotide to facilitate insertion of the donor polynucleotide with the cleaved target polynucleotide. In some embodiments the donor polynucleotide may express a polypeptide once inserted into the target polynucleotide. In certain embodiments, the polypeptide can be a protein that can function to induce cell differentiation or maturation to proceed in a particular manner, such as toward a specific lineage. In certain embodiments, the expression of a polypeptide by the donor polynucleotide may be controlled by an inducible promoter. In other embodiments, the expression of a polypeptide by the donor polynucleotide may be controlled by a repressible promoter. In other embodiments the donor polynucleotide may encode more than one polypeptide, for example, the donor polynucleotide may include an expression cassette having a plurality of genes. In certain embodiments wherein the donor polynucleotide encodes more than one polypeptide, the donor polynucleotide may have inducible promoters to regulate the expression of certain genes and repressible promoters to regulate the expression of other genes.

In certain embodiments, the donor polynucleotide is a single-stranded or double-stranded donor polynucleotide with sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, such that the polynucleotide is introduced into the genome of the cell. In certain embodiments, the overhangs are from about 15 bases to about 500 bases. In certain embodiments, the overhangs are at least 15 nucleotides in length, such as 20, 30, 40, 50, 60, 70, 80, 90, 100, 200, 300, 400, 500, 600, 700, 800, 900, or 1,000 bases. In certain embodiments, the overhangs are at least 15 bases, alternatively at least 20 bases, alternatively at least 25 bases, alternatively at least 30 bases, alternatively at least 35 bases, alternatively at least 40 bases, alternatively at least 50 bases, alternatively at least 55 bases, alternatively at least 60 bases, alternatively at least 65 bases, alternatively at least 70 bases, alternatively at least 75 bases, alternatively at least about 100 bases, alternatively at least about 150 bases, alternatively at least about 200 bases, alternatively at least about 300 bases, alternatively at least about 400 bases, alternatively at least about 500 bases, alternatively at least about 800 bases. The complementarity need not be 100% complementarity. For example, the complementary overhangs can be 95%, 96%, 97%, 98%, or 99% complementary to the overhangs of the cleaved target polynucleotide.

In certain embodiments, the methods include inserting a donor polynucleotide into the genome of a cell. The donor polynucleotide can be of any length, such as between about 10 and about 10,000 nucleotides in length (or any integer value inbetween), such as between about 50 and about 2,000 nucleotides in length, or between about 100 and about 1,000 nucleotides in length (or any integer there between), or between about 200 and about 500 nucleotides in length. Techniques for determining nucleic acid and amino acid sequence identity are known in the art.

F. Dual Guide RNA Method

Figure 6:
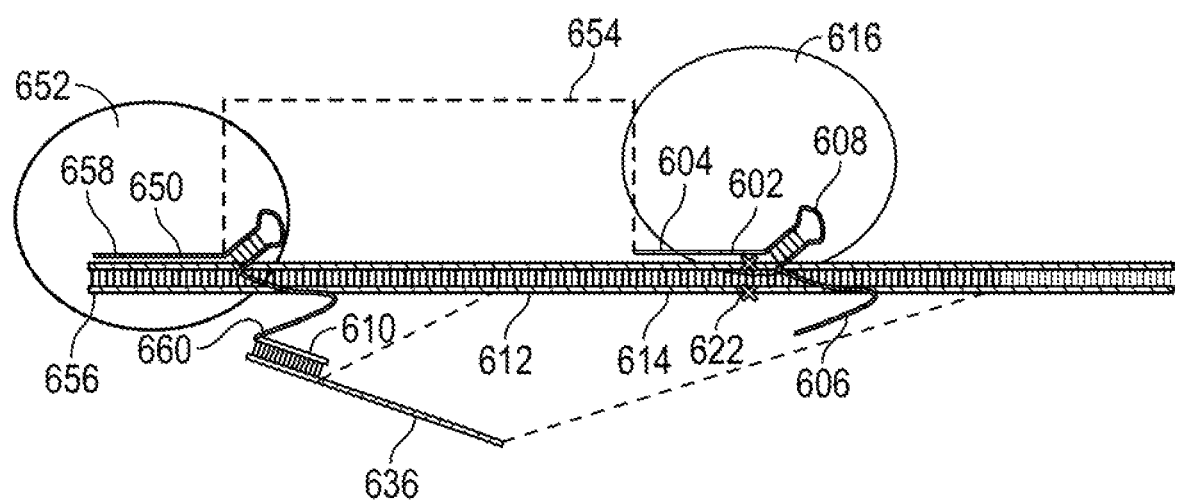
FIG. 6 illustrates a dual guide RNA method and compositions to localize donor DNA to vicinity of Cas9 break site.

FIG. 6 illustrates a dual guide RNA strategy to localize a donor polynucleotide to the vicinity of a Cas-catalyzed break site. More particularly, FIG. 6 shows a strategy two guide RNAs 602, 650, a Cas9 enzyme 616, and a catalytically inactive Cas9 mutant (dCas9). A first single-guide RNA 602 has a crRNA domain 604 containing a guide sequence, which is complementary to a first target sequence 614 in a target polynucleotide 612, a tracrRNA domain 606 that binds the Cas9 enzyme 616, and a hairpin or duplex structure 608 between the crRNA 604 and tracrRNA 606. The Cas9:first guide RNA complex binds a first target sequence 614 containing a protospacer directly upstream of a PAM site. At the first target sequence 614 in the target polynucleotide 612, a double-strand break (DSB) is made by Cas9 cleaving at the site 622 indicated by arrows. A second single-guide RNA 650 has a crRNA domain 658 at the 5' end, which is complementary to a second target sequence 656 in the target polynucleotide 612, a tracrRNA domain 660 that binds the dCas9 mutant 652. The second single-guide RNA 650 also comprises a first adaptor segment 610 that is attached to a donor single-stranded polynucleotide 636. The dCas9:second guide RNA complex binds but does not cleave the second target sequence 656.

The Cas9:first guide RNA (sgRNA1) complex cuts at the correct target polynucleotide site 622, while the second guide RNA (sgRNA2) 650 is tethered to the donor DNA 636 (single-stranded here) and binds to a nearby second target sequence, separated by an offset 654 from the first target sequence 614. In this instance, the second guide RNA is loaded by a catalytically inactive Cas9 (dCas9) 652 and thus does not cleave or nick the DNA. The sgRNA1:Cas9 mediated DSB at the target polynucleotide initiates DNA repair mechanism, with a higher likelihood of homologous recombination due to the nearby presence of the donor DNA 636.

The functionality of the tethered donor polynucleotide as a template for HR may be retained when complexed to the guide RNA and Cas9 protein by a tethering configuration. However, the mechanism of Cas9-mediated HR has not been fully elicited, and the means by which the guide RNA:Cas9 complex is removed from double-stranded break (DSB) site in the DNA, after cleavage is not yet characterized. It is contemplated that prior to, or in the course of the HR repair of the DSB, involves degradation or sequestration of guide RNA:Cas9 complex away from the DSB. In this situation, donor DNA tethered to the guide RNA:Cas9 would not stay localized to the DSB or may be degraded. In situations where the HR event is found to be destructive to the guide RNA:Cas9 complex, a dual guide RNA approach may be preferred for Cas-based HR, having a second guide RNA:dCas9 (catalytically inactive) complex, binding a DNA sequence near the target of the first guide RNA:Cas9 complex (FIG. 6). The first guide RNA does not contain an adaptor sequence and this guide RNA:Cas9 complex functions to make the DSB at the desired target site, while the second guide RNA has an adaptor and is tethered to the donor DNA. Regardless of the fate of the first guide RNA:Cas9 complex after it makes a DSB, the (second) guide RNA:donor DNA:dCas9 complex will remain in the vicinity of the DSB prior and during DNA repair, providing a localized donor polynucleotide to bias repair towards HR pathways.

The distance or length of the offset 654 (in base pairs) between the DNA target sequences of the dual guide RNAs should be selected so that the targets are far enough apart that they do not interfere with each other's functionality or HR events, while close enough that the tethered donor DNA at the offset target can be effectively used as a HR template when a DSB is made at the target site by the first guide RNA:Cas9 complex. Selection of appropriate offset distances is informed by published research evaluating offset ranges for paired nickases, which similarly require dual sgRNA:Cas9 function independently in close proximity on a target DNA sequence (See, e.g., Mall et al., CAS9 transcriptional activators for target specificity screening and paired nickases for cooperative genome engineering. Nature Biotechnology 31, 833-838(2013); Ran et al., Double Nicking by RNA-Guided CRISPR Cas9 for Enhanced Genome Editing Specificity. Cell, 154(6), 1380-1389 (2013)).

For example, the offset can range from at least −8 bp to 100 bp, alternatively from −4 bp to 20 bp, alternatively from 0 bp to 12 bp. In certain embodiments, the offset is at least −8 bp, at least −6 bp, at least −4 bp, or at least 2 bp, or at least 0 bp, or at least 2 bp, or at least 4 bp. In certain embodiments, the offset is at most 100 bp, or at most 60 bp, or at most 40 bp, or at most 30 bp, or at most 20 bp, or at most 18 bp, or at most 16 bp, or at most 14 bp, or at most 12 bp, or at most 10 bp, or at most 8 bp. Any of the foregoing minima and maxima may be combined to form a range. A negative offset means guide sequences overlap by that many base pairs; an offset of −4 indicates that the first guide sequence binds to 4 nucleotides in a first strand of the target polynucleotide that are base paired with nucleotides in the complemetary sequence bound by the second guide sequence.

This strategy requires the guide RNA:donor DNA to complex with dCas9, while the cleavage-targeting guide RNA to complex with a catalytically active Cas9 protein. To ensure this, one possibility is to employ orthogonal Cas9 proteins (Esvelt et al., Orthogonal Cas9 proteins for RNA-guided gene regulation and editing. Nat Methods. 2013 November; 10(11):1116-21 (2013)), which can be introduced to the cell as plasmid, mRNA or protein, specifically loading the desired guide RNA. Alternatively, each guide RNA can be pre-complexed with respective Cas9 protein in vitro before delivery into a cell, in this way ensuring that the guide RNA:donor DNA is loaded into dCas9. Lastly in some instances, if both guide RNA targets are within the sequence covered by the HR template, either cut should be repaired by HR and both cuts may infact increase HR, as has been observed in stem cells gene editing (Mandal et al., Efficient ablation of genes in human hematopoietic stem and effector cells using CRISPR/Cas9. Cell Stem Cell. November 6; 15(5):643-52 (2014).

Another dual guide RNA strategy for localizing a donor polynucleotide to the vicinity of a Cas-catalyzed break site involves the use of a truncated guide sequence. More particularly, the strategy employs a first guide RNA that targets and hybridizes to a first target sequence of a target polynucleotide. The first guide RNA is adapted to form a complex with a catalytically active Cas9 protein, thereby forming a catalytically active complex. The strategy also employs a second guide RNA that targets and hybridizes to a second target sequence of the target polynucleotide, thereby forming a complex with a catalytically active Cas9 protein. However, the second guide RNA has a truncated guide sequence, and the Cas9:second gRNA complex is not catalytically active. The truncated guide sequence of the second guide RNA comprises 14, 15 or 16 nucleotides. While the inventors are not to be bound by theory, it is believed that a truncated guide RNA having 14, 15 or 16 nucleotides will retain its abilities to form a complex with Cas proteins, to recognize with a complementary target sequence, and to bind that target sequence; however the complex formed by the Cas protein and a 14 nt gRNA, 15 nt gRNA or 16 nt gRNA will not substantially cleave or nick the target sequence, in that little or no cleavage or nicking is detectable. In Fu et al., Nat. Biotechnol., 32, 279-84 (2014), improvement in the specificity of CRISPR-Cas9 cleavage was achieved by truncating the 20-nt guide sequence by 2 or 3 nucleotides at its 5' end to generate truncated guide RNAs (tru-RGNs). Off-target cleavage activity was reduced by these tru-RGNs having 17 or 18 nucleotides complementary to a target sequence. However, additional truncation of the 5' end generally reduces on-target guide RNA-Cas9 activity, reducing it to background levels when the DNA-pairing sequence is truncated to 15 nt or shorter, and substantially decreasing or eliminating detectable activity when truncated to 16 nt. The desired length of the truncated gRNA may be selected based on the genetic target (including the nature of the organism and the target polynucleotide), based on different organismal Cas9 proteins, or based on both of the foregoing.

In this dual gRNA strategy, the second gRNA has a crRNA domain at the 5' end comprising the truncated guide sequence, a tracrRNA domain at the 3' end that binds a Cas9 protein, and a first adaptor segment attached to the 5' end or the 3' end. The first adaptor segment is complementary to (i) a donor polynucleotide, (ii) a second adaptor segment, or (iii) a splint segment. The first adaptor segment can be attached directly or indirectly to a donor polynucleotide. The Cas protein:second guide RNA complex binds but does not cleave a second target sequence. The first target sequence and the second target sequence can have an offset between them, as described above, resulting in the second gRNA brings the donor polynucleotide in a desired proximity to the cleavage site made by the Cas9:first gRNA complex, thereby increasing the likelihood of homologous recombination. Advantages of this dual gRNA strategy are that it does not require orthogonal Cas9 proteins, nor does it require a dCas9 or other "dead" Cas protein, nor does it require more than one Cas protein.

G. Synthesis of Guide RNA

In certain embodiments, guide RNAs, including single guide RNAs (sgRNAs; see FIGS. 1 and 2B) are produced by chemical synthesis using the art of synthetic organic chemistry. A guide RNA that comprises any nucleotide other than the four predominant ribonucleotides, namely A, C, G, and U, whether unnatural or natural, such as a pseudouridine, inosine or a deoxynucleotide, possesses a chemical modification or substitution at the nucleotide which is chemically/structurally distinct from any of the four predominant nucleotides in RNAs.

The synthetic guide RNAs described herein can be chemically synthesized. For example, the synthetic guide RNAs can be synthesized using TC chemistry by the methods described in Dellinger et al., J. Am. Chem. Soc. 2011, 133, 11540, U.S. Pat. No. 8,202,983, and US Patent Application 2010/0076183A1, the contents of which are incorporated by reference in their entireties. "TC chemistry" refers to the composition and methods of using RNA monomeric nucleotide precursors protected on the 2'-hydroxyl moiety by a thionocarbamate protecting group, to synthesize unmodified RNA or modified RNA comprising one or more modified nucleotides. The ability to chemically synthesize relatively long RNAs (as long as 200 nucleotides or more) using TC-RNA chemistry allows one to produce guide RNAs with special features capable of outperforming those enabled by the four predominant ribonucleotides (A, C, G and U). Some synthetic guide RNAs described herein can also be made using methods known in the art that include in vitro transcription and cell-based expression. For example, 2'-fluoro NTPs can be incorporated into synthetic guide RNAs produced by cell-based expression.

Synthesis of guide RNAs can also be accomplished by chemical or enzymatic synthesis of RNA sequences that are subsequently ligated together by enzymes, or chemically ligated by chemical ligation, including but not limited to cyanogen bromide chemistry, "click" chemistry as published by R. Kumar, et al., in Journal of the American Chemical Society, 2007, 129, 6859-6864, or squarate conjugation chemistry as described by K. Hill in WO2013176844 titled "Compositions and methods for conjugating oligonucleotides."

As further described below, a guide RNA disclosed herein, including those comprising adaptor segments with modified nucleotides and/or modified internucleotide linkages, can be used to perform various CRISPR-mediated functions (including but not limited to editing genes, regulating gene expression, cleaving target sequences, and binding to target sequences) in vitro or in vivo, such as in cell-free assays, in intact cells, or in whole organisms. For in vitro or in vivo applications, the RNA can be delivered into cells or whole organisms in any manner known in the art.

H. Libraries of Guide RNAs

In one aspect, the present invention provides a set or library of multiple guide RNAs having adaptor segments. In certain embodiments, the library contains two or more guide RNAs disclosed herein. The library can contain from about 10 to about $10^7$ individual members, e.g., about 10 to about $10^2$, about $10^2$ to about $10^3$, about $10^3$ to about $10^5$, from about $10^5$ to about $10^7$ members. An individual member of the library differs from other members of the library at least in the guide sequence, i.e., the DNA targeting segment of the gRNA. On the other hand, in certain embodiments, each individual member of a library can contain the same or substantially the same nucleotide sequence for the tracrRNA segment and/or adaptor segment as all the other members of the library. In this way, the library can comprise members that target different polynucleotides or different sequences in one or more polynucleotides.

In certain embodiments, the library comprises at least $10^2$ unique guide sequences. In certain embodiments, the library comprises at least $10^3$ unique guide sequences. In certain embodiments, the library comprises at least $10^4$ unique guide sequences. In certain embodiments, the library comprises at least $10^5$ unique guide sequences. In certain embodiments, the library comprises at least $10^6$ unique guide sequences. In certain embodiments, the library comprises at least $10^7$ unique guide sequences. In certain embodiments, the library targets at least 10 different polynucleotides. In certain embodiments, the library targets at least $10^2$ different polynucleotides. In certain embodiments, the library targets at least $10^3$ different polynucleotides. In certain embodiments, the library targets at least $10^4$ different polynucleotides. In certain embodiments, the library targets at least $10^5$ different polynucleotides. In certain embodiments, the library targets at least $10^6$ different polynucleotides. In certain embodiments, the library targets at least $10^7$ different polynucleotides.

In certain embodiments, the library allows one to conduct high-throughput, multi-target genomic manipulations and analyses. In certain embodiments, only the DNA-targeting segments of the guide RNAs are varied, while the Cas protein-binding segment is the same. In certain embodiments, a first portion of the library comprises guide RNAs possessing a Cas-binding segment that recognizes, binds and directs a particular Cas protein and a second portion of the library comprises a different Cas-binding segment that recognizes, binds and directs a different Cas protein (e.g., a Cas protein from a different species), thereby allowing the library to function with two or more orthogonal Cas proteins. In certain embodiments, induced expression of a first orthogonal Cas protein utilizes the portion of the library which interacts with the first orthogonal Cas protein. In certain embodiments, induced expression of a first and second orthogonal Cas protein utilizes the portions of the library which interact with the first and second orthogonal Cas proteins, respectively. In certain embodiments, induced expression of the first and second orthogonal Cas proteins occur at different times. Accordingly, one can carry out large-scale gene editing or gene regulation by specifically manipulating or modifying multiple targets as specified in the library.

IV. Cas Proteins

As mentioned above, a functional CRISPR-Cas system also requires a protein component (e.g., a Cas protein, which may be a Cas nuclease) that provides a desired activity, such as target binding or target nicking/cleaving. In certain embodiments, the desired activity is target binding. In certain embodiments, the desired activity is target nicking or target cleaving. The Cas protein can be introduced into an in vitro or in vivo system as a purified or non-purified (i) Cas protein or (ii) mRNA encoded for expression of the Cas protein or (iii) linear or circular DNA encoded for expression of the protein. Any of these three methods of providing the Cas protein are well known in the art and are implied interchangeably when mention is made herein of a Cas protein or use of a Cas protein. In certain embodiments, the Cas protein is constitutively expressed from mRNA or DNA. In certain embodiments, the expression of Cas protein from mRNA or DNA is inducible or induced.

In certain embodiments, the Cas protein is chemically synthesized (see e.g., Creighton, "Proteins: Structures and Molecular Principles," W.H. Freeman & Co., NY, 1983), or produced by recombinant DNA technology as described herein. For additional guidance, skilled artisans may consult Frederick M. Ausubel et al., Current Protocols in Molecular Biology, John Wiley & Sons, 2003; and Sambrook et al., Molecular Cloning, A Laboratory Manual," Cold Spring Harbor Press, Cold Spring Harbor, N.Y., 2001).

In certain embodiments, the Cas protein is provided in purified or isolated form. In certain embodiments, the Cas protein is provided at about 80%, about 90%, about 95%, or about 99% purity. In certain embodiments, the Cas protein is provided as part of a composition. In certain embodiments, the Cas protein is provided in aqueous compositions suitable for use as, or inclusion in, a composition for an RNA-guided nuclease reaction. Those of skill in the art are well aware of the various substances that can be included in such nuclease reaction compositions.

In certain embodiments, a Cas protein is provided as a recombinant polypeptide. In certain examples, the recombinant polypeptide is prepared as a fusion protein. For example, in certain embodiments, a nucleic acid encoding the Cas protein is linked to another nucleic acid encoding a fusion partner, e.g., glutathione-s-transferase (GST), 6x-His epitope tag, or M13 Gene 3 protein. Suitable host cells can be used to expresses the fusion protein. In certain embodiments, the fusion protein is isolated by methods known in the art. In certain embodiments, the fusion protein can be further treated, e.g., by enzymatic digestion, to remove the fusion partner and obtain the Cas protein. Alternatively, Cas protein:guide RNA complexes can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties.

A. Wild Type Cas Proteins

In certain embodiments, a Cas protein comprises a protein of or derived from a CRISPR-Cas type I, type II, or type III system, which has an RNA-guided polynucleotide-binding or nuclease activity. Non-limiting examples of suitable Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966. See e.g., WO2014144761 WO2014144592, WO2013176772, US20140273226, and US20140273233, the contents of which are incorporated herein by reference in their entireties.

In certain embodiments, the Cas protein is derived from a type II CRISPR-Cas system. In certain embodiments, the Cas protein is or is derived from a Cas9 protein. In certain embodiments, the Cas protein is or is derived from a bacterial Cas9 protein, including those identified in WO2014144761. In certain embodiments, the Cas protein is or is derived from a *Streptococcus* sp. or *Staphylococcus* sp. Cas9 protein. In certain embodiments, the Cas protein is or is derived from the *Streptococcus thermophilus* Cas9 protein. In certain embodiments, the Cas protein is or is derived from a the *Streptococcus pyogenes* Cas9 protein. In certain embodiments, the Cas protein is or is derived from the *Staphylococcus aureus* Cas9 protein. In certain embodiments, the Cas protein is or is derived from the *Streptococcus thermophilus* Cas9 protein.

In certain embodiments, the wild type Cas protein is a Cas9 p. In certain embodiments, the wild type Cas9 protein is the Cas9 protein from *S. pyogenes* (SEQ ID NO:1). In certain embodiments, the protein or polypeptide can comprise, consist of, or consist essentially of a fragment of SEQ ID NO:1.

In general, a Cas protein includes at least one RNA binding domain, which interacts with the guide RNA. In certain embodiments, the Cas protein is modified to increase nucleic acid binding affinity and/or specificity, alter an enzymatic activity, and/or change another property of the protein. For example, nuclease (i.e., DNase, RNase) domains of the Cas protein can be modified, mutated, deleted, or inactivated. Alternatively, the Cas protein can be truncated to remove domains that are not essential for the function of the protein. In certain embodiments, the Cas protein is truncated or modified to optimize the activity of the effector domain. In certain embodiments, the Cas protein includes a nuclear localization sequence (NLS) that effects importation of the NLS-tagged Cas protein into the nucleus of a living cell. In certain embodiments, the Cas protein includes two or more modifications.

B. Mutant Cas Proteins

In some embodiments, the CRISPR protein can be a mutant of a wild type CRISPR protein (such as Cas9) or a fragment thereof. Examples of known mutants of Cas9 include the Cas9 nickases such as Cas9-D10A, cleavage-deactivated dCas9, Cas9 mutants with altered PAM specificity such as those disclosed in Kleinstiver et al., "Engineered CRISPR-Cas9 nucleases with altered PAM specificities", Nature 523,481-.485 (2015) (e.g., D1135E SpCas9), Cas9 mutants from *Staphylococcus aureus* (Sa-Cas9) such as those disclosed in Ran et al., "In vivo genome editing using *Staphylococcus aureus* Cas9", Nature 520, 186-191 (2015). In other embodiments, the CRISPR protein can be derived from a mutant CRISPR protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein. In some embodiments, the present system utilizes the Cas9 protein from *S. pyogenes*, either as encoded in bacteria or codon-optimized for expression in mammalian cells. Shown below is the amino acid sequence of wild type *S pyogenes* Cas9 protein sequence (SEQ ID NO: 1, available at www.uniprot.org/uniprot/Q99ZW2), sometimes referred to as (SpCas9).

(SEQ ID NO: 1)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIdGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIERRLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

LANGEIKRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

A Cas9 protein generally has at least two nuclease (e.g., DNase) domains. For example, a Cas9 protein can have a RuvC-like nuclease domain and an HNH-like nuclease domain. The RuvC and HNH domains work together to cut both strands in a target site to make a double-stranded break in the target polynucleotide. (Jinek et al., Science, 337: 816-821). In certain embodiments, a mutant Cas9 protein is modified to contain only one functional nuclease domain (either a RuvC-like or an HNH-like nuclease domain). For example, in certain embodiments, the mutant Cas9 protein is modified such that one of the nuclease domains is deleted or mutated such that it is no longer functional (i.e., the nuclease activity is absent). In some embodiments where one of the nuclease domains is inactive, the mutant is able to introduce a nick into a double-stranded polynucleotide (such protein is termed a "nickase") but not able to cleave the double-stranded polynucleotide. For example, an aspartate to alanine (D10A) conversion in a RuvC-like domain converts the Cas9-derived protein into a nickase. Likewise, a histidine to alanine (H840A) conversion in a HNH domain converts the Cas9-derived protein into a nickase. Likewise, an arsparagine to alanine (N863A) conversion in a HNH domain converts the Cas9-derived protein into a nickase.

In certain embodiments, both the RuvC-like nuclease domain and the HNH-like nuclease domain are modified or eliminated such that the mutant Cas9 protein is unable to nick or cleave the target polynucleotide. In certain embodiments, all nuclease domains of the Cas9-derived protein are modified or eliminated such that the Cas9-derived protein lacks all nuclease activity. In certain embodiments, a Cas9 protein that lacks some or all nuclease activity relative to a wild-type counterpart, nevertheless, maintains target recognition activity to a greater or lesser extent.

A catalytically inactivate Cas9 protein may interchangeably be referred to as a "dCas9" protein (for nuclease "dead" Cas9). In some embodiments, dCas9 corresponds to, or comprises in part or in whole, the Cas9 mutant D10A and H840A are provided, which e.g., result in nuclease inactivated Cas9 (dCas9). Such mutations, by way of example, include other amino acid substitutions at D10 and H840, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO:5) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:5. In some embodiments, variants of dCas9 (e.g., variants of SEQ ID NO:5) are provided having amino acid sequences which are shorter, or longer than SEQ ID NO:5, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

This present compositions and methods can be used with CRISPR protein other than *S. pyogenes* Cas9, including other Cas proteins from bacteria or archaea as well as Cas9 variants that nick a single strand of DNA or have no nuclease activity, such as the above-mentioned cleavage-deactivated Cas9 bearing catalysis-inactivating mutations in one or both nuclease domains. This method can be applied to systems that utilize a single guide RNA as well as those that use dual RNAs (e.g., the crRNA and tracrRNA activities found in naturally occurring systems).

In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In certain embodiments, the "Cas mutant" or "Cas variant" is at least 50% (e.g., any number between 50% and 100%, inclusive, e.g., 50%, 60%, 70%, 80%, 90%, 95%, 98%, and 99%) identical to SEQ ID NO:1. In certain embodiments, the "Cas mutant" or "Cas variant" binds to an RNA molecule (e.g., a sgRNA). In certain embodiments, the "Cas mutant" or "Cas variant" is targeted to a specific polynucleotide sequence via the RNA molecule.

CRISPR/Cas protein-guide RNA complexes can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties. The complexes can be isolated or purified, at least to some extent, from cellular material of a cell or an in vitro translation-transcription system in which they are produced.

V. Uses and Methods

In one aspect, the present invention provides a method for cleaving a target polynucleotide with a Cas protein. The method comprises contacting the target polynucleotide with (i) a guide RNA or a set of guide RNA molecules described herein, and (ii) a Cas protein. In certain embodiments, the method results in a double-strand break in the target polynucleotide. In certain embodiments, the Cas protein is a Cas protein having a single-strand nicking activity. In certain embodiments, the method results in a single-strand break in the target polynucleotide. In certain embodiments, a complex comprising a guide RNA and Cas protein having a single-strand nicking activity is used for sequence-targeted single-stranded DNA cleavage, i.e., nicking. In some embodiments, the method comprises contacting the target polynucleotide with two Cas proteins; in some of those embodiments, each of the two Cas proteins has a single strand nicking activity.

In one aspect, the present invention provides a method for binding two or more target polynucleotides with a Cas protein. The method comprises contacting the target polynucleotides with (i) a set of RNA molecules described herein and (ii) a Cas protein, to result in binding of the target polynucleotides with the Cas protein. In certain embodiments, the method comprises two Cas proteins, wherein one of the Cas protein is a Cas variant that lacks some or all nuclease activity relative to a counterpart wild-type Cas protein and the other Cas protein has double-strand cleaving activity.

In one aspect, the present invention provides a method for targeting a Cas protein to a target polynucleotide. The method comprises contacting the Cas protein with a guide RNA or a set of guide RNA molecules described herein. In certain embodiments, the method results in formation of a guide RNA:Cas protein complex. In certain embodiments, the Cas protein is a wild type Cas9 protein. In certain embodiments, the Cas protein is a mutant or variant of a Cas9 protein. In certain embodiments, the Cas protein is a Cas protein having a single-strand nicking activity. In certain embodiments, the Cas protein is a Cas protein lacking nuclease activity (e.g., a nuclease-deficient mutant of Cas protein). In certain embodiments, the Cas protein is part of a fusion protein (e.g., a fusion protein comprising (i) the Cas protein or and (ii) a heterologous polypeptide).

In one aspect, the present invention provides a method for targeting a Cas protein to two or more target polynucleotides. The method comprises contacting the Cas protein with a set of guide RNA molecules described herein. In certain embodiments, the method results in formation of a guide RNA:Cas protein complex. In certain embodiments, the Cas protein is a wild type Cas9 protein. In certain embodiments, the Cas protein is a mutant or variant of a Cas9 protein. In certain embodiments, the Cas protein is a Cas protein having a single-strand nicking activity. In certain embodiments, the Cas protein is a Cas protein lacking nuclease activity (e.g., a nuclease-deficient mutant of Cas protein). In certain embodiments, the Cas protein is part of a fusion protein (e.g., a fusion protein comprising (i) the Cas protein or and (ii) a heterologous polypeptide).

In certain embodiments, the guide RNA is introduced into a cell by transfection. Techniques for RNA transfection are known in the art and include electroporation and lipofection. Effective techniques for RNA transfection depend mostly on cell type. See, e.g., Lujambio et al. (Spanish National Cancer Centre) Cancer Res. February 2007, which described transfection of HTC-116 colon cancer cells and used Oligofectamine (Invitrogen) for transfection of commercially obtained, modified miRNA or precursor miRNA. See also, Cho et al. (Seoul National Univ.) Nat. Biotechnol. March 2013, which described transfection of K562 cells and used 4D Nucleofection™ (Lonza) electroporation for transfection of transcribed sgRNAs (about 60 nts long). Techniques for transfection of RNA are also known in the art. For example, therapeutic RNA has been delivered in non-pathogenic E. coli coated with Invasin protein (to facilitate uptake into cells expressing β-1 integrin protein) and with the E. coli encoded to express lysteriolysin O pore-forming protein to permit the shRNA to pass from the E. coli into the cytoplasm. See also Cho et al. (Seoul National Univ.) Nat. Biotechnol. March 2013.

In certain embodiments, the guide RNA is introduced or delivered into cells. Technologies that can be used for delivery of guide RNA include those that utilize encapsulation by biodegradable polymers, liposomes, or nanoparticles. Such polymers, liposomes, and nanoparticles can be delivered intravenously. In certain embodiments, for in vivo delivery, guide RNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781, which are hereby incorporated by reference in their entirety. In certain embodiments, guide RNA or a delivery vehicle containing guide RNA is targeted to a particular tissue or body compartment. For example, in certain embodiments, to target exogenous RNA to other tissues, synthetic carriers are decorated with cell-specific ligands or aptamers for receptor uptake, e.g., RNA encased in cyclodextrin nanoparticles coated w/PEG and functionalized with human transferrin protein for uptake via the transferrin receptor which is highly expressed in tumor cells. Further approaches are described herein below or known in the art.

In certain embodiments, the method and compositions described above can be used for modifying a chromosomal sequence in a cell, embryo, or animal. The method comprises contacting or introducing into the cell or embryo (a) one or more RNA-guided endonucleases or nucleic acid encoding the RNA-guided endonucleases and (b) one or more guide RNAs or DNA encoding the guide RNAs, wherein the guide RNA leads the endonuclease to a targeted site in the chromosomal sequence and the RNA-guided endonuclease cleaves at least one strand of the chromosomal sequence at the targeted site. The target site can contain or be next to a mutation, e.g., point mutation, a translocation or an inversion which may cause or is associated with a disorder. To correct such a mutation, in some embodiments, the method further comprises contacting or introducing into the cell or embryo at least one donor polynucleotide comprising a wild type counterpart of the mutation and at least one sequence having substantial sequence identity with sequence on one side of the targeted site in the chromosomal sequence.

In certain embodiments, the method and compositions described above can be used for modifying a mammalian cell, including but not limited to in primary cells, stem cells, immortalized cells, and conditionally immortalized cells. Among the phenotypes of cells suitable for the present method and guide RNA are chondrocytes, diabetic cells, epithelial cells, fibroblasts, gastrointestinal cells, hematopoietic stem/progenitor and immune cells, hepatocytes, keratinocytes, melanocytes, neural cells, progenitor cells, renal cells, skeletal muscle cells, smooth muscle cells, sertoli cells, and others.

A. Genome Editing

In one aspect, the present invention provides a method for genomic editing to modify a DNA sequence in vivo or in vitro ("in vitro" includes, without being limited to, a cell-free system, a cell lysate, an isolated component of a cell, and a cell outside of a living organism). The DNA sequence may comprise a chromosomal sequence, an episomal sequence, a plasmid, a mitochondrial DNA sequence, or a functional intergenic sequence, such as an enhancer sequence or a non-coding RNA. The method comprises contacting the DNA sequence with (i) a guide RNA or a set of guide RNA molecules described herein, and (ii) a Cas protein. In certain embodiments, the DNA sequence is contacted outside of a cell. In certain embodiments, the DNA sequence is located in the genome within a cell and is contacted in vitro or in vivo. In certain embodiments, the cell is within an organism or tissue. In certain embodiments, the cell is a human cell, a non-human mammalian cell, a stem cell, a non-mammalian vertebrate cell, an invertebrate cell, a plant cell, a single cell organism, or an embryo. In certain embodiments, the guide RNA aids in targeting the Cas protein to a targeted site in the DNA sequence. In certain embodiments, the Cas protein cleaves at least one strand of the DNA sequence at the targeted site. In certain embodiments, the Cas protein cleaves both strands of the DNA sequence at the targeted site.

In certain embodiments, the method further comprises introducing the Cas protein into a cell or another system. In certain embodiments, the Cas protein is introduced as a purified or non-purified protein. In certain embodiments, the Cas protein is introduced via an mRNA encoding the Cas protein. In certain embodiments, the Cas protein is introduced via a linear or circular DNA encoding the Cas protein. In certain embodiments, the cell or system comprises a Cas protein or a nucleic acid encoding a Cas protein.

In certain embodiments, a double-stranded break can be repaired by a homology-directed repair (HDR) process such that a donor polynucleotide in a donor polynucleotide can be integrated into or exchanged with the targeted DNA sequence.

In certain embodiments, the method further comprises introducing at least one donor polynucleotide into the cell or system. In certain embodiments, the donor polynucleotide comprises at least one homologous sequence having substantial sequence identity with a sequence on either side of the targeted site in the DNA sequence. In certain embodiments, the donor polynucleotide comprises a donor polynucleotide that can be integrated into or exchanged with the DNA sequence via homology-directed repair, such as homologous recombination.

In certain embodiments, the donor polynucleotide includes an upstream homologous sequence and a downstream homologous sequence, each of which have substantial sequence identity to sequences located upstream and downstream, respectively, of the targeted site in the DNA sequence. These sequence similarities permit, for example, homologous recombination between the donor polynucleotide and the targeted DNA sequence such that the donor polynucleotide can be integrated into (or exchanged with) the DNA sequence targeted.

In certain embodiments, the target site(s) in the DNA sequence spans or is adjacent to a mutation, e.g., point mutation, a translocation or an inversion which may cause or be associated with a disorder. In certain embodiments, the method comprises correcting the mutation by introducing into the cell or system at least one donor polynucleotide comprising (i) a wild type counterpart of the mutation and (ii) at least one homologous sequence having substantial sequence identity with a sequence on one side of the targeted site in the DNA sequence. In certain embodiments, the donor polynucleotide comprises a homologous sequence having substantial sequence identity with a sequence on both sides of the targeted site in the DNA sequence.

In certain embodiments, the donor polynucleotide comprises an exogenous sequence that can be integrated into or exchanged with the targeted DNA sequence via a homology-directed repair process, such as homologous recombination. In certain embodiments, the exogenous sequence comprises a protein coding gene, which, optionally, is operably linked to an exogenous promoter control sequence. Thus, in certain embodiments, upon integration of the exogenous sequence, a cell can express a protein encoded by the integrated gene. In certain embodiments, the exogenous sequence is integrated into the targeted DNA sequence such that its expression in the recipient cell or system is regulated by the exogenous promoter control sequence. Integration of an exogenous gene into the targeted DNA sequence is termed a "knock in." In other embodiments, the exogenous sequence can be a transcriptional control sequence, another expression control sequence, an RNA coding sequence, or another functional sequence.

In certain embodiments, the donor polynucleotide comprises a sequence that is essentially identical to a portion of the DNA sequence at or near the targeted site, but comprises at least one nucleotide change. For example, in certain embodiments, the donor polynucleotide comprises a modified or mutated version of the DNA sequence at or near the targeted site such that, upon integration or exchange with the targeted site, the resulting sequence at the targeted site comprises at least one nucleotide change. In certain embodiments, the at least one nucleotide change is an insertion of one or more nucleotides, a deletion of one or more nucleotides, a substitution of one or more nucleotides, or combinations thereof. As a consequence of the integration of the modified sequence, the cell may produce a modified gene product from the targeted DNA sequence.

In certain embodiments, the compounds and methods are for multiplex applications. In certain embodiments, a library of guide RNAs is provided or introduced into the cell or system. In certain embodiments, the library comprises at least 100 unique guide sequences. In certain embodiments, the library comprises at least 1,000 unique guide sequences. In certain embodiments, the library comprises at least 10,000 unique guide sequences. In certain embodiments, the library comprises at least 100,000 unique guide sequences. In certain embodiments, the library comprises at least 1,000,000 unique guide sequences. In certain embodiments, the library targets at least 10 different polynucleotides or at least 10 different sequences within one or more polynucleotides. In certain embodiments, the library targets at least 100 different polynucleotides or at least 100 different sequences within one or more polynucleotides. In certain embodiments, the library targets at least 1,000 different polynucleotides or at least 1,000 different sequences within one or more polynucleotides. In certain embodiments, the library targets at least 10,000 different polynucleotides or at least 10,000 different sequences within one or more polynucleotides. In certain embodiments, the library targets at least 100,000 different polynucleotides or at least 100,000 different sequences within one or more polynucleotides. In certain embodiments, the library targets at least 1,000,000 different polynucleotides or at least 1,000,000 different sequences within one or more polynucleotides.

In certain embodiments, compounds and methods are provided for multiplex applications wherein a plurality of orthogonal adaptor segments on guide RNA sequences are used to tether different donor polynucleotides. Each of the orthogonal adaptor segments is part of a guide RNA having a different crRNA. This enables the plurality of guide RNAs to specifically bind to unique cognate donor polynucleotides, enabling editing of a plurality of target polynucleotides via HR in a cell. Applications of this multiplex genome editing approach could be simultaneous targeted amino acid substitutions in the functional groups of enzymes such as kinases, or engineering multiple splice donor or acceptor sites to alter the steady state pool of mRNA isoforms.

VI. Kits

In one aspect, the present invention provides kits containing reagents for performing the above-described methods, including producing gRNA:Cas protein complex and/or supporting its activity for binding, or cleaving target polynucleotide. In certain embodiments, one or more of the reaction components, e.g., one or more guide RNAs and Cas proteins, for the methods disclosed herein, can be supplied in the form of a kit for use. In certain embodiments, the kit comprises a Cas protein or a nucleic acid encoding the Cas protein, and one or more guide RNAs described herein or a set or library of guide RNAs. In certain embodiments, the kit comprises a donor polynucleotide. In certain embodiments, the kit includes one or more other reaction components. In certain embodiments, an appropriate amount of one or more reaction components is provided in one or more containers or held on a substrate.

Examples of additional components of the kits include, but are not limited to, one or more different polymerases, one or more host cells, one or more reagents for introducing foreign nucleic acid into host cells, one or more reagents (e.g., probes or PCR primers) for detecting expression of the guide RNA and/or the Cas mRNA or protein or for verifying the status of the target nucleic acid, and buffers, transfection reagents or culture media for the reactions (in 1X or more concentrated forms). In certain embodiments, the kit includes one or more of the following components: biochemical and physical supports; terminating, modifying and/or digesting reagents; osmolytes; and apparati for reaction, transfection and/or detection.

The reaction components used can be provided in a variety of forms. For example, the components (e.g., enzymes, RNAs, probes and/or primers) can be suspended in an aqueous solution or bound to a bead or as a freeze-dried or lyophilized powder or pellet. In the latter case, the components, when reconstituted, form a complete mixture of components for use in an assay. The kits of the invention can be provided at any suitable temperature. For example, for storage of kits containing protein components or complexes thereof in a liquid, it is preferred that they are provided and maintained below 0° C., preferably at about −20° C., possibly in a freeze-resistant solution containing glycerol or other suitable antifreeze.

A kit or system may contain, in an amount sufficient for at least one homologous recombination, any combination of the components described herein. In some applications, one or more reaction components may be provided in pre-measured single use amounts in individual, typically disposable, tubes or equivalent containers. With such an arrangement, a RNA-guided nuclease reaction can be performed by adding a target nucleic acid, or a sample or cell containing the target nucleic acid, to the individual tubes directly. The amount of a component supplied in the kit can be any appropriate amount and may depend on the market to which the product is directed. The container(s) in which the components are supplied can be any conventional container that is capable of holding the supplied form, for instance, microfuge tubes, microtiter plates, ampules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

EXEMPLARY EMBODIMENTS

Exemplary embodiments provided in accordance with the presently disclosed subject matter include, but are not limited to, the claims and the following embodiments:

A1. A synthetic guide RNA comprising:
a crRNA segment comprising (i) a guide sequence capable of hybridizing to a target sequence, (ii) a stem sequence;
a tracrRNA segment comprising a nucleotide sequence that is partially or completely complementary to the stem sequence; and
a first adaptor segment comprising a sequence complementary to (i) a donor polynucleotide, (ii) a second adaptor segment, or (iii) a splint segment,
wherein the adaptor sequence comprises one or more stability-enhancing modifications; and
wherein the synthetic guide RNA has gRNA functionality.

A2. The synthetic guide RNA of embodiment A1, wherein at least one of the modifications is a modification that increases resistance of the adaptor sequence to RNase H cleavage.

A3. The synthetic guide RNA of embodiment A1 or A2, wherein the adaptor sequence comprises one or more 2-O-methyl moieties.

A4. The synthetic guide RNA of embodiment A1 or A2, wherein the adaptor sequence comprises one or more phosphorothioate groups.

A5. The synthetic guide RNA of embodiment A1 or A2, wherein the adaptor sequence comprises one or more phosphonoacetate (PACE) groups.

A6. The synthetic guide RNA of embodiment A1 or A2, wherein the adaptor sequence comprises one or more thiophosphonoacetate (thioPACE) groups.

A7. The synthetic guide RNA of embodiment A1 or A2, whereas the modification in the adaptor segment comprises a 2'-O-methyl moiety, a 2'-fluoro moiety, a 2'-deoxy moiety, a phosphorothioate internucleotide linkage, a phosphonoacetate internucleotide linkage, a thiophosphonoacetate internucleotide linkage, or combinations thereof.

A8. The synthetic guide RNA of embodiment A or A2, wherein the adaptor segment comprises one or more modifications selected from the group consisting of a 2'-O-methyl nucleotide with a 3'-phosphorothioate group, a 2'-O-methyl nucleotide with a 3'-phosphonocarboxylate group, a 2'-O-methyl nucleotide with a 3'-phosphonoacetate group, a 2'-O-methyl nucleotide with a 3'-thiophosphonocarboxylate group, a 2'-O-methyl nucleotide with a 3'-thiophosphonoacetate group, a 2'-deoxy nucleotide with a 3'-phosphonoacetate group, and a 2'-deoxy nucleotide with a 3'-thiophosphonoacetate group.

A9. The synthetic guide RNA of embodiment A1 or A2, wherein the stability-enhancing modification comprises a 2'-O-methyl moiety, a 2'-fluoro moiety, or a 2'-deoxy moiety.

A10. The synthetic guide RNA of embodiment A1 or A2, wherein the stability-enhancing modification comprises a phosphorothioate internucleotide linkage, a phosphonoacetate internucleotide linkage, a thiophosphonoacetate internucleotide linkage, a methylphosphonate internucleotide linkage, a boranophosphate internucleotide linkage, or a phosphorodithioate internucleotide linkage.

A11. The synthetic guide RNA of embodiment A1 or A2, wherein the stability-enhancing modification comprises a 2'-O-methyl,3'-phosphorothioate nucleotide, a 2'-O-methyl, 3'-phosphonoacetate nucleotide, or a 2'-O-methyl,3'-thiophosphonoacetate nucleotide.

A12. The synthetic guide RNA of embodiment A1 or A2, wherein the stability-enhancing modification comprises a 2'-fluoro,3'-phosphorothioate nucleotide, a 2'-fluoro,3'-phosphonoacetate nucleotide, or a 2'-fluoro,3'-thiophosphonoacetate nucleotide.

A13. The synthetic guide RNA of any of the preceding embodiments, wherein the stability-enhancing modification comprises more than one of the stability-enhancing modifications.

A14. The synthetic guide RNA of any of the preceding embodiments, wherein the adaptor segment is linked to the tracrRNA segment, and one of the stability-enhancing modifications is located within the last five nucleotides of the adaptor segment.

A15. The synthetic guide RNA of any of the preceding embodiments, wherein the first adaptor segment is an RNA sequence.

A16. The synthetic guide RNA of any of the preceding embodiments, wherein the second adaptor segment is a DNA sequence.

A17. The synthetic guide RNA of any of the preceding embodiments, wherein the adaptor segment is attached to a donor polynucleotide by base-pair hybridization.

A18. The synthetic guide RNA of any one of embodiments A1-A16, wherein the adaptor segment is attached to a donor polynucleotide by an internucleotide linkage.

A19. The synthetic guide RNA of any one of the preceding embodiments, wherein the synthetic guide RNA is a single guide RNA, wherein the crRNA segment and the tracrRNA segment are linked.

A20. The synthetic guide RNA of any one of the preceding embodiments, wherein the crRNA segment is at the 5' end of the guide RNA and the adaptor segment is attached (i) to the crRNA segment or (ii) to a 5' overhang attached to the 5' end of the crRNA segment.

A21. The synthetic guide RNA of any one of the preceding embodiments, wherein the tracrRNA segment is at the 3' end of the guide RNA and the adaptor segment is attached (i) to the tracrRNA segment or (ii) to a 3' overhang attached to the 3' end of the tracrRNA segment.

A22. The synthetic guide RNA of any of the preceding embodiments, wherein the crRNA segment comprises from 25 to 70 nucleotides.

A23. The synthetic guide RNA of any of the preceding embodiments, wherein the guide sequence comprises from 15 to 30 nucleotides.

A24. The synthetic guide RNA of any of the preceding embodiments, wherein the stem sequence comprises from 10 to 50 nucleotides.

A25. The synthetic guide RNA of any of the preceding embodiments, where the adaptor segment is from 10 to 40 nucleotides.

B1. A guide RNA:donor polynucleotide complex, comprising (a) a synthetic guide RNA having gRNA functionality and (b) a donor polynucleotide,
wherein the synthetic guide RNA comprises:
a crRNA segment comprising (i) a guide sequence capable of hybridizing to a target sequence, (ii) a stem sequence;
a tracrRNA segment comprising a nucleotide sequence that is partially or completely complementary to the stem sequence; and
a first adaptor segment comprising a sequence complementary to (i) a donor polynucleotide, (ii) a second adaptor segment, or (iii) a splint segment, and the adaptor sequence comprises one or more stability-enhancing modifications; and
the donor polynucleotide is attached to one of the first adaptor segment, the second adaptor segment, or the splint segment.

B2. The guide RNA:donor polynucleotide complex of embodiment B1, wherein the donor polynucleotide is attached to the first adaptor segment by base-pairing hybridization.

B3. The guide RNA:donor polynucleotide complex of embodiment B1, wherein the donor polynucleotide is attached to the first adaptor segment by an internucleotide linkage.

B4. The guide RNA:donor polynucleotide complex of embodiment B1, wherein the first adaptor segment is attached by base-pairing hybridization to the second adaptor segment, and the second adaptor segment is attached to the donor polynucleotide by an internucleotide linkage.

B5. The guide RNA:donor polynucleotide complex of embodiment B4, wherein the first adaptor segment is an RNA sequence, and the second adaptor segment is a DNA sequence.

B6. The guide RNA:donor polynucleotide complex of embodiment 84, wherein the donor polynucleotide is single-stranded DNA.

B7. The guide RNA:donor polynucleotide complex of embodiment B4, wherein the donor polynucleotide is double-stranded DNA.

B8. The guide RNA:donor polynucleotide complex of embodiment B1, wherein the first adaptor segment is attached by base-pairing hybridization to a splint segment, and the splint segment is attached by base-pairing hybridization to the donor polynucleotide.

C1. A method for editing a target polynucleotide comprising:

contacting the target polynucleotide with a CRISPR-associated protein and the synthetic guide RNA or guide RNA:donor polynucleotide complex of any one of the preceding embodiments, cleaving the target polynucleotide, and joining a donor polynucleotide to the target polynucleotide.

C2. The method of embodiment C1, further comprising contacting the target polynucleotide with an exogenous CRISPR-associated protein.

C3. The method of embodiment C2, wherein the CRISPR-associated protein is Cas9.

C4. The method of any one of embodiments C1 to C3, further comprising repairing the cleaved target polynucleotide by homology-directed repair with the donor polynucleotide.

C5. The method of embodiment C4, wherein the donor polynucleotide comprises at least one sequence having substantial sequence identity with a sequence on either side of the cleavage site.

C6. The method of any one of embodiments C4 to C5, wherein the joining step produces an insertion, deletion, or substitution of one or more nucleotides of the target polynucleotide.

C7. The method of embodiment C6, wherein the insertion, deletion, or substitution results in one or more amino acid changes in a protein expressed from a gene comprising the target polynucleotide.

C8. The method of any one of embodiments C1 to C7, wherein the target polynucleotide is contacted with the CRISPR-associated protein and the synthetic guide RNA or guide RNA:donor polynucleotide complex in vitro.

C9. The method of any one of embodiments C1 to C8, wherein the target polynucleotide contacted with the CRISPR-associated protein and the synthetic guide RNA or guide RNA:donor polynucleotide complex is within the genome of a cell in vitro or in vivo.

C10. The method of embodiment C9, wherein the cell is isolated from a multicellular source prior to contacting the target polynucleotide with the CRISPR-associated protein and the synthetic guide RNA.

C11. The method of embodiment C10, wherein the source is a plant, an animal, a multicellular protist, or a fungus.

C12. The method of any one of embodiments C9 to C11, wherein the cell, or a cell derived therefrom, is returned to the source after contacting the target polynucleotide with the CRISPR-associated protein and the synthetic guide RNA.

D1. A method of modifying a target polynucleotide in a cell comprising introducing into the cell (a) the synthetic guide RNA of any one of embodiments A1 to A25; (b) one or more donor polynucleotides; and (c) a CRISPR-associated protein or a nucleic acid that expresses a CRISPR-associated protein in the cell.

D2. A method of modifying a target polynucleotide in a cell comprising introducing into the cell (a) the guide RNA:donor polynucleotide complex of any one of embodiments B1 to B8 and (b) a CRISPR-associated protein or a nucleic acid that expresses a CRISPR-associated protein in the cell.

D3. The method of embodiment D1 or D2, wherein the CRISPR-associated-protein is Cas9.

D4. A set or library of RNA molecules comprising two or more synthetic guide RNAs of any one of embodiments A1 to A25.

D5. The set or library of RNA molecules of embodiment D4, wherein the set or library comprises a plurality of orthogonal adaptor segments on the synthetic guide RNAs, wherein the adaptor segments adapted for tethering different donor polynucleotides.

D6. The set or library of RNA molecules of embodiment D4, wherein the set or library comprises a plurality of synthetic guide RNAs, each of which has a unique crRNA and a unique adaptor segments adapted for tethering different donor polynucleotides, enabling editing of a plurality of target polynucleotides via HR in a cell.

E1. A kit comprising (a) the synthetic guide RNAs of any one of embodiments A1 to A25, or (b) the guide RNA:donor polynucleotide complex of any one of embodiments B1 to B8; or (c) the set or library of RNA molecules of any one of embodiments D1 to D6; or (d) combinations thereof.

E2. The kit of embodiment E1 or E2, further comprising one or more donor polynucleotides.

E3. The kit of embodiment E1 or E2, further comprising a CRISPR-associated protein or a nucleic acid encoding the CRISPR-associated protein.

E4. The kit of embodiment E3, wherein the CRISPR-associated-protein is Cas9.

E5. The kit of any one of embodiments E1 to E4, further comprising instructions for using in a genome editing method: (a) the synthetic guide RNAs of any one of embodiments A1 to A25, or (b) the guide RNA:donor polynucleotide complex of any one of embodiments B1 to B8; or (c) the set or library of RNA molecules of any one of embodiments D1 to D6.

F1. A method of inserting exogenous DNA into a genome of a cell using homologous recombination, comprising introducing into the cell (a) the synthetic guide RNA of any one embodiments A1 to A25; or (b) the guide RNA:donor polynucleotide complex of any one of embodiments B1 to B8.

G1. A CRISPR-Cas system for use in homologous recombination of a target polynucleotide, the system comprising:

a Cas protein; and a synthetic guide RNA comprising:

a crRNA segment comprising (i) a guide sequence capable of hybridizing to a target sequence, (ii) a stem sequence;

a tracrRNA segment comprising a nucleotide sequence that is partially or completely complementary to the stem sequence; and a first adaptor segment comprising a sequence complementary to (i) a donor polynucleotide, (ii) a second adaptor segment, or (iii) a splint segment, wherein the adaptor sequence comprises one or more stability-enhancing modifications; and wherein the synthetic guide RNA has gRNA functionality.

G2. The system of embodiment G1, wherein the Cas protein is catalytically inactive.

G3. The system of embodiment G1, wherein the guide sequence is 17, 18, 19 or 20 nucleotides in length.

G4. The system of embodiment G1, wherein the guide sequence is 14, 15 or 16 nucleotides in length.

H1. A CRISPR-Cas system for homologous recombination of a target polynucleotide, the system comprising:
a catalytically active Cas protein;
a first guide RNA that targets and hybridizes to a first target sequence of a target polynucleotide, wherein the first guide RNA forms a complex with the catalytically active Cas protein;
a catalytically inactive Ca9 protein;
a second guide RNA that targets and hybridizes to a second target sequence of the target polynucleotide, wherein the second guide RNA forms a complex with the catalytically inactive Cas protein, and wherein the second guide RNA comprises a first adaptor segment.

H2. The system of embodiment H1, wherein the first target sequence and the second target sequence are in a same strand or in opposite strands of a double-stranded target polynucleotide, and an offset of −8 to 100 base pairs separates the first target sequence and the second target sequence.

H3. The system of embodiment H1 or H2, wherein the first adaptor segment is attached to (i) a donor polynucleotide; (ii) a second adaptor segment; or (iii) a splint segment.

H4. The system of embodiment H3, wherein the first adaptor segment is attached to a second adaptor segment by base-pairing, and the second adaptor segment is attached to a donor polynucleotide.

H5. The system of embodiment H4, wherein the second adaptor segment is attached to a donor polynucleotide by an internucleotide linkage.

H6. The system of embodiment H1 or H2, wherein the first adaptor segment is attached to a donor polynucleotide by a splint segment, and the splint segment has first and second portions,
wherein the first portion is attached to the first adaptor by hybridization of complementary base pairs, and the second portion is attached to the donor polynucleotide by hybridization of complementary base pairs.

H7. The system of any of embodiments H1 to H6, wherein the first adaptor segment has one or more stability-enhancing modifications.

H8. The system of any of embodiments H1 to H7, wherein the catalytically active Cas protein is Cas9, a Cas9 mutant, or a Cas9 variant.

H9. The system of any of embodiments H1 to H8, wherein the catalytically inactive Cas protein is dCas9.

I1. A CRISPR-Cas system for homologous recombination of a target polynucleotide, the system comprising:
a Cas protein;
a first guide RNA that targets and hybridizes to a first target sequence of a target polynucleotide, wherein the first guide RNA forms a complex with the Cas protein;
a second guide RNA that is 14, 15 or 16 nucleotides in length and is complementary to a second target sequence of the target polynucleotide, wherein the second guide RNA forms a complex with the Cas protein, and the second guide RNA comprises a first adaptor segment,
wherein the Cas protein:second guide RNA complex recognizes and binds the second target sequence but the complex is catalytically inactive.

I2. The system of embodiment I1, wherein the first target sequence and the second target sequence are in a same strand or in opposite strands of a double-stranded target polynucleotide, and an offset of −8 to 100 base pairs separates the first target sequence and the second target sequence.

I3. The system of embodiment I1 or I2, wherein the first adaptor segment is attached to (i) a donor polynucleotide; (ii) a second adaptor segment; or (iii) a splint segment.

I4. The system of embodiment I3, wherein the first adaptor segment is attached to a second adaptor segment by base-pairing, and the second adaptor segment is attached to a donor polynucleotide.

I5. The system of embodiment I4, wherein the second adaptor segment is attached to a donor polynucleotide by an internucleotide linkage.

I6. The system of embodiment I1 or I2, wherein the first adaptor segment is attached to a donor polynucleotide by a splint segment, and the splint segment has first and second portions,
wherein the first portion is attached to the first adaptor by hybridization of complementary base pairs, and the second portion is attached to the donor polynucleotide by hybridization of complementary base pairs.

I7. The system of any of embodiments I1 to I6, wherein the first adaptor segment has one or more stability-enhancing modifications.

I8. The system of any of embodiments I1 to H7, wherein the Cas protein is Cas9, a Cas9 mutant, or a Cas9 variant.

The foregoing description of exemplary or preferred embodiments should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

We claim:

1. A synthetic guide RNA comprising:
a crRNA segment comprising (i) a guide sequence capable of hybridizing to a target sequence, (ii) a stem sequence;
a tracrRNA segment comprising a nucleotide sequence that is partially or completely complementary to the stem sequence; and
a first adaptor segment comprising a sequence complementary to (i) a donor polynucleotide, (ii) a second adaptor segment, or (iii) a splint segment, wherein the first adaptor segment is attached to a 5' end of the crRNA or to a 3' end of the tracrRNA,
wherein the first adaptor segment comprises one or more modifications selected from the group consisting of 2'-O—C$_1$-C$_4$ alkyl, 2'-deoxy (2'-H), 2'-halo, 2'-amino ("2'-NH$_2$"), 2'-arabinosyl ("2'-arabino") nucleotide, 2'-F-arabinosyl ("2'-F-arabino") nucleotide, 2'-locked nucleic acid ("LNA") nucleotide, 2'-unlocked nucleic acid ("ULNA") nucleotide, L-sugar, 4'-thioribosyl nucleotide, phosphorothioate (P(S)), phosphonocarboxylate (P(CH$_2$)$_n$COOR), thiophosphonocarboxylate ((S)P(CH$_2$)$_n$COOR), alkylphosphonate (P(C$_1$-C$_3$ alkyl), boranophosphonate (P(BH$_3$)), and phosphorodithioate (P(S)$_2$).

2. The synthetic guide RNA of claim 1, wherein at least one of the modifications is a modification that increases resistance of the first adaptor segment to RNase H cleavage.

3. The synthetic guide RNA of claim 1, wherein the modification in the first adaptor segment comprises a 2'-O-methyl moiety, a 2'-fluoro moiety, a 2'-deoxy moiety, a phosphorothioate internucleotide linkage, a phosphonoacetate internucleotide linkage, a thiophosphonoacetate internucleotide linkage, or combinations thereof.

4. The synthetic guide RNA of claim 1, wherein the first adaptor segment comprises one or more modifications selected from the group consisting of a 2'-O-methyl nucleotide with a 3'-phosphorothioate group, a 2'-O-methyl nucleotide with a 3'-phosphonocarboxylate group, a 2'-O-methyl nucleotide with a 3'-phosphonoacetate group, a 2'-O-methyl nucleotide with a 3'-thiophosphonocarboxylate group, a 2'-O-methyl nucleotide with a 3'-thiophosphonoacetate group, a 2'-deoxy nucleotide with a 3'-phosphonoacetate group, and a 2'-deoxy nucleotide with a 3'-thiophosphonoacetate group.

5. The synthetic guide RNA of claim 1, wherein the first adaptor segment is linked to the tracrRNA segment, and one of the stability-enhancing modifications is located within the last five nucleotides of the first adaptor segment.

6. The synthetic guide RNA of claim 1, wherein the first adaptor segment is an RNA sequence.

7. The synthetic guide RNA of claim 1, wherein the second adaptor segment is a DNA sequence.

8. The synthetic guide RNA of claim 1, wherein the splint segment is a DNA sequence.

9. A guide RNA:donor polynucleotide complex, comprising (a) a synthetic guide RNA according to claim 1, and (b) a donor polynucleotide,
the donor polynucleotide being attached to one of the first adaptor segment, the second adaptor segment, or the splint segment.

10. The guide RNA:donor polynucleotide complex of claim 9, wherein the donor polynucleotide is attached to the first adaptor segment, the second adaptor segment, or the splint segment by base-pairing hybridization.

11. The guide RNA:donor polynucleotide complex of claim 9, wherein the donor polynucleotide is attached to the first adaptor segment, the second adaptor segment, or the splint segment by an internucleotide linkage.

12. The guide RNA:donor polynucleotide complex of claim 9, wherein the first adaptor segment is attached by base-pairing hybridization to a splint segment, and the splint segment is attached by base-pairing hybridization to the donor polynucleotide.

13. A method for editing a target polynucleotide comprising:
contacting the target polynucleotide with a CRISPR-associated protein and the synthetic guide RNA of claim 1,
cleaving the target polynucleotide, and
joining the donor polynucleotide to the target polynucleotide.

14. The method of claim 13, further comprising contacting the target polynucleotide with an exogenous CRISPR-associated protein.

15. The method of claim 14, wherein the CRISPR-associated protein is Cas9.

16. The method of claim 13, further comprising repairing the cleaved target polynucleotide by homology-directed repair with the donor polynucleotide.

17. The method of claim 16, wherein the donor polynucleotide comprises at least one sequence having substantial sequence identity with a sequence on either side of the cleavage site.

18. The method of claim 13, wherein the target polynucleotide is contacted with the CRISPR-associated protein and the synthetic guide RNA in vitro.

19. A method of modifying a target polynucleotide in a cell comprising introducing into the cell (a) the synthetic guide RNA of claim 1; (b) the donor polynucleotide; and (c) a CRISPR-associated protein or a nucleic acid that expresses a CRISPR-associated protein in the cell.

20. A method of modifying a target polynucleotide in a cell comprising introducing into the cell (a) the guide RNA:donor polynucleotide complex of claim 9; and (b) a CRISPR-associated protein or a nucleic acid that expresses a CRISPR-associated protein in the cell.

* * * * *